United States Patent
Zerhusen

(10) Patent No.: US 10,206,836 B2
(45) Date of Patent: *Feb. 19, 2019

(54) BED EXIT ALERTS FOR PERSON SUPPORT APPARATUS

(71) Applicant: Hill-Rom Services, Inc., Batesville, IN (US)

(72) Inventor: Robert Mark Zerhusen, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/798,839

(22) Filed: Oct. 31, 2017

(65) Prior Publication Data

US 2018/0049932 A1 Feb. 22, 2018

Related U.S. Application Data

(63) Continuation of application No. 14/356,041, filed as application No. PCT/US2012/064692 on Nov. 12, 2012, now Pat. No. 9,827,156.

(Continued)

(51) Int. Cl.
*A61G 7/05* (2006.01)
*G08B 5/00* (2006.01)
(Continued)

(52) U.S. Cl.
CPC ............. *A61G 7/05* (2013.01); *A61G 7/0514* (2016.11); *A61G 7/0516* (2016.11);
(Continued)

(58) Field of Classification Search
CPC ................ A61G 12/00; A61G 2203/12; A61G 2203/72; A61G 7/012; A61G 7/0516; A61G 7/053
See application file for complete search history.

(56) References Cited

U.S. PATENT DOCUMENTS 1,078,077 A 11/1913 Arnold
2,527,111 A 10/1950 Widrich
(Continued)

FOREIGN PATENT DOCUMENTS

EP 0860803 A2 8/1998
EP 1199027 A2 4/2002
(Continued)

OTHER PUBLICATIONS

Hill-Rom "Duo Deteq Alternating Therapy System User Manual (usr037)", Oct. 2000.
(Continued)

*Primary Examiner* — Omeed Alizada
(74) *Attorney, Agent, or Firm* — Barnes & Thornburg LLP

(57) ABSTRACT

A person support apparatus with an extendable mattress, a night light message display system, a screen key pendant, egress handle siderails, and various other features. The extendable mattress includes hinged extensions along the sides of the extendable mattress that are moved from a nested position to the extension position. The screen key pendant includes a plurality of screen keys that can be pressed to cycle through various control modes for the person support apparatus. The night light message display system can be configured to display a message or image on the floor communicating information to the person and/or alerting the person as to when they are able to exit the bed.

20 Claims, 48 Drawing Sheets

Related U.S. Application Data

(60) Provisional application No. 61/559,035, filed on Nov. 11, 2011.

(51) Int. Cl.
  *A61G 12/00* (2006.01)
  *A61G 7/012* (2006.01)
  *A61G 7/015* (2006.01)
  *A61G 7/018* (2006.01)
  *A61G 7/053* (2006.01)
  *G06F 19/00* (2018.01)
  *G16H 40/63* (2018.01)

(52) U.S. Cl.
  CPC ............ *A61G 7/0528* (2016.11); *A61G 12/00* (2013.01); *G06F 19/00* (2013.01); *G08B 5/00* (2013.01); *G16H 40/63* (2018.01); *A61G 7/012* (2013.01); *A61G 7/015* (2013.01); *A61G 7/018* (2013.01); *A61G 7/053* (2013.01); *A61G 7/0506* (2013.01); *A61G 2200/16* (2013.01); *A61G 2203/12* (2013.01); *A61G 2203/70* (2013.01); *A61G 2203/72* (2013.01)

(56) References Cited

U.S. PATENT DOCUMENTS

| | | |
|---|---|---|
| 3,325,799 A | 6/1967 | Farris |
| 3,504,540 A | 4/1970 | Lee et al. |
| 3,618,592 A | 11/1971 | Stewart |
| 3,697,846 A | 10/1972 | Mueller |
| 3,760,794 A | 9/1973 | Basham |
| 3,802,417 A | 4/1974 | Lang |
| 3,826,145 A | 7/1974 | McFarland |
| 3,836,900 A | 9/1974 | Mansfield |
| 3,890,958 A | 6/1975 | Fister et al. |
| 3,898,981 A | 8/1975 | Basham |
| 3,926,177 A | 12/1975 | Hardway, Jr. et al. |
| 3,961,201 A | 6/1976 | Rosenthal |
| 3,991,414 A | 11/1976 | Moran |
| 3,991,746 A | 11/1976 | Hanna |
| 4,020,482 A | 4/1977 | Feldl |
| 4,038,709 A | 8/1977 | Kerwit |
| 4,051,522 A | 9/1977 | Healy et al. |
| 4,097,939 A | 7/1978 | Peck et al. |
| 4,172,216 A | 10/1979 | O'Shea |
| 4,175,263 A | 11/1979 | Morrow et al. |
| 4,179,692 A | 12/1979 | Vance |
| 4,183,015 A | 1/1980 | Drew et al. |
| 4,195,287 A | 3/1980 | Mathis et al. |
| 4,196,425 A | 4/1980 | Weekly et al. |
| 4,197,854 A | 4/1980 | Kasa |
| 4,228,426 A | 10/1980 | Roberts |
| 4,242,672 A | 12/1980 | Gault |
| 4,245,651 A | 1/1981 | Frost |
| 4,264,904 A | 4/1981 | McCoy et al. |
| 4,275,385 A | 6/1981 | White |
| 4,295,133 A | 10/1981 | Vance |
| 4,320,766 A | 3/1982 | Alihanka et al. |
| 4,426,884 A | 1/1984 | Polchaninoff |
| 4,435,862 A | 3/1984 | King et al. |
| 4,484,043 A | 11/1984 | Musick et al. |
| 4,539,560 A | 9/1985 | Fleck et al. |
| 4,561,440 A | 12/1985 | Kubo et al. |
| 4,565,910 A | 1/1986 | Musick et al. |
| 4,592,104 A | 6/1986 | Foster et al. |
| 4,601,356 A | 7/1986 | Muccillo |
| 4,633,237 A | 12/1986 | Tucknott et al. |
| 4,638,307 A | 1/1987 | Swartout |
| 4,669,136 A | 6/1987 | Waters et al. |
| 4,680,790 A | 7/1987 | Packard et al. |
| 4,700,180 A | 10/1987 | Vance |
| 4,751,754 A | 6/1988 | Bailey et al. |
| 4,793,428 A | 12/1988 | Swersey |
| 4,803,744 A | 2/1989 | Peck et al. |
| 4,907,845 A | 3/1990 | Wood |
| 4,921,295 A | 5/1990 | Stollenwerk |
| 4,926,951 A | 5/1990 | Carruth et al. |
| 4,934,468 A | 6/1990 | Koerber et al. |
| 4,947,298 A | 8/1990 | Stephen |
| 4,953,243 A | 9/1990 | Birkmann |
| 4,953,244 A | 9/1990 | Koerber et al. |
| 4,974,692 A | 12/1990 | Carruth et al. |
| 4,998,939 A | 3/1991 | Potthast et al. |
| 5,010,774 A | 4/1991 | Kikuo et al. |
| 5,023,967 A | 6/1991 | Ferrand |
| 5,060,174 A | 10/1991 | Gross |
| 5,115,223 A | 5/1992 | Moody |
| 5,117,521 A | 6/1992 | Foster et al. |
| 5,137,033 A | 8/1992 | Norton |
| 5,138,729 A | 8/1992 | Ferrand |
| 5,144,284 A | 9/1992 | Hammett |
| 5,161,274 A | 11/1992 | Hayes et al. |
| 5,170,364 A | 12/1992 | Gross et al. |
| 5,184,112 A | 2/1993 | Gusakov |
| 5,195,198 A | 3/1993 | Travis |
| 5,239,300 A | 8/1993 | Berger et al. |
| 5,253,656 A | 10/1993 | Rincoe et al. |
| 5,269,388 A | 12/1993 | Reichow et al. |
| 5,276,432 A | 1/1994 | Travis |
| 5,279,010 A | 1/1994 | Ferrand et al. |
| 5,307,051 A | 4/1994 | Sedlmayr |
| 5,317,769 A | 6/1994 | Weismiller et al. |
| 5,353,012 A | 10/1994 | Barham et al. |
| 5,377,372 A | 1/1995 | Rudolf et al. |
| 5,393,935 A | 2/1995 | Hasty et al. |
| 5,410,297 A | 4/1995 | Joseph et al. |
| 5,444,880 A | 8/1995 | Weismiller et al. |
| 5,450,639 A | 9/1995 | Weismiller et al. |
| 5,502,853 A | 4/1996 | Singleton et al. |
| 5,542,138 A | 8/1996 | Williams et al. |
| 5,561,412 A | 10/1996 | Novak et al. |
| 5,611,096 A | 3/1997 | Bartlett et al. |
| 5,633,627 A | 5/1997 | Newham |
| 5,640,145 A | 6/1997 | Newham |
| 5,654,694 A | 8/1997 | Newham |
| 5,689,839 A | 11/1997 | Laganiere et al. |
| 5,699,038 A | 12/1997 | Ulrich et al. |
| 5,713,856 A | 2/1998 | Eggers et al. |
| 5,715,548 A | 2/1998 | Weismiller et al. |
| 5,771,511 A | 6/1998 | Kummer et al. |
| 5,774,914 A | 7/1998 | Johnson et al. |
| 5,806,111 A | 9/1998 | Heimbrock et al. |
| 5,808,552 A | 9/1998 | Wiley et al. |
| 5,830,149 A | 11/1998 | Oka et al. |
| 5,838,223 A | 11/1998 | Gallant et al. |
| 5,878,452 A | 3/1999 | Brooke et al. |
| 5,906,016 A | 5/1999 | Ferrand et al. |
| 6,000,076 A | 12/1999 | Webster et al. |
| 6,008,598 A | 12/1999 | Luff et al. |
| 6,014,346 A | 1/2000 | Malone |
| 6,014,784 A | 1/2000 | Taylor et al. |
| 6,021,533 A | 2/2000 | Ellis et al. |
| 6,049,281 A | 4/2000 | Osterweil |
| 6,057,689 A | 5/2000 | Saadat |
| 6,067,019 A | 5/2000 | Scott |
| 6,078,261 A | 6/2000 | Davsko |
| 6,147,592 A | 11/2000 | Ulrich et al. |
| 6,163,903 A | 12/2000 | Weismiller et al. |
| 6,166,644 A | 12/2000 | Stroda |
| 6,188,407 B1 | 2/2001 | Smith et al. |
| 6,199,508 B1 | 3/2001 | Miale et al. |
| 6,208,250 B1 | 3/2001 | Dixon et al. |
| 6,226,819 B1 | 5/2001 | Ogawa et al. |
| 6,234,642 B1 | 5/2001 | Bokmper |
| 6,240,579 B1 | 6/2001 | Hanson et al. |
| 6,252,512 B1 | 6/2001 | Riley |
| 6,279,183 B1 | 8/2001 | Kummer et al. |
| 6,286,166 B1 | 9/2001 | Henley et al. |
| 6,320,510 B2 | 11/2001 | Menkedick et al. |
| 6,321,878 B1 | 11/2001 | Mobley et al. |
| 6,336,235 B1 | 1/2002 | Ruehl |
| 6,351,861 B1 | 3/2002 | Shows et al. |
| 6,362,725 B1 | 3/2002 | Ulrich et al. |

(56) References Cited

U.S. PATENT DOCUMENTS

| | | |
|---|---|---|
| 6,377,178 B1 | 4/2002 | DeToro et al. |
| 6,378,152 B1 | 4/2002 | Washburn et al. |
| 6,396,224 B1 | 5/2002 | Luff et al. |
| 6,430,766 B1 | 8/2002 | Henley et al. |
| 6,467,111 B1 | 10/2002 | Vrzalik et al. |
| 6,473,921 B2 | 11/2002 | Brooke et al. |
| 6,481,688 B1 | 11/2002 | Welling et al. |
| 6,493,568 B1 | 12/2002 | Bell et al. |
| 6,544,200 B1 | 4/2003 | Smith et al. |
| 6,566,833 B2 | 5/2003 | Bartlett |
| 6,611,979 B2 | 9/2003 | Welling et al. |
| 6,658,680 B2 | 12/2003 | Osborne et al. |
| 6,671,905 B2 | 1/2004 | Bartlett et al. |
| 6,691,346 B2 | 2/2004 | Osborne et al. |
| 6,761,344 B2 | 7/2004 | Welling et al. |
| 6,771,172 B1 | 8/2004 | Robinson et al. |
| 6,771,181 B1 | 8/2004 | Hughen |
| 6,781,517 B2 | 8/2004 | Moster et al. |
| 6,791,460 B2 | 9/2004 | Dixon et al. |
| 6,819,254 B2 | 11/2004 | Riley |
| 6,822,571 B2 | 11/2004 | Conway |
| 6,829,796 B2 | 12/2004 | Salvatini et al. |
| 6,863,652 B2 | 3/2005 | Huang et al. |
| 6,876,303 B2 | 4/2005 | Reeder et al. |
| 6,880,189 B2 | 4/2005 | Welling et al. |
| 6,892,405 B1 | 5/2005 | Dimitriu et al. |
| 6,897,780 B2 | 5/2005 | Ulrich et al. |
| 6,957,461 B2 | 10/2005 | Osborne et al. |
| 6,978,500 B2 | 12/2005 | Osborne et al. |
| 6,982,405 B2 | 1/2006 | Erickson et al. |
| 7,010,369 B2 | 3/2006 | Borders et al. |
| 7,014,000 B2 | 3/2006 | Kummer et al. |
| 7,017,208 B2 | 3/2006 | Weismiller et al. |
| 7,033,028 B1 | 4/2006 | Belliveau |
| 7,038,588 B2 | 5/2006 | Boone et al. |
| 7,055,195 B2 | 6/2006 | Roussy |
| 7,100,222 B2 | 9/2006 | Metz et al. |
| 7,154,397 B2 | 12/2006 | Zerhusen et al. |
| 7,155,317 B1 | 12/2006 | Tran |
| 7,171,708 B2 | 2/2007 | Osborne et al. |
| 7,200,882 B2 | 4/2007 | Heimbrock |
| 7,237,287 B2 | 7/2007 | Weismiller et al. |
| 7,242,308 B2 | 7/2007 | Ulrich et al. |
| 7,253,366 B2 | 8/2007 | Bhai |
| 7,296,312 B2 | 11/2007 | Menkedick et al. |
| 7,315,535 B2 | 1/2008 | Schuman |
| 7,319,386 B2 | 1/2008 | Collins, Jr. et al. |
| 7,330,127 B2 | 2/2008 | Price et al. |
| 7,406,731 B2 | 8/2008 | Menkedick et al. |
| 7,437,787 B2 | 10/2008 | Bhai |
| 7,443,302 B2 | 10/2008 | Reeder et al. |
| 7,454,805 B2 | 11/2008 | Osborne et al. |
| 7,472,439 B2 | 1/2009 | Lemire et al. |
| 7,480,951 B2 | 1/2009 | Weismiller et al. |
| 7,506,390 B2 | 3/2009 | Dixon et al. |
| 7,515,059 B2 | 4/2009 | Price et al. |
| 7,520,006 B2 | 4/2009 | Menkedick et al. |
| 7,533,429 B2 | 5/2009 | Menkedick et al. |
| 7,538,659 B2 | 5/2009 | Ulrich et al. |
| 7,557,718 B2 | 7/2009 | Petrosenko et al. |
| 7,568,246 B2 | 8/2009 | Weismiller et al. |
| 7,594,286 B2 | 9/2009 | Williams |
| 7,610,637 B2 | 11/2009 | Menkedick et al. |
| 7,657,956 B2 | 2/2010 | Stacy et al. |
| 7,669,263 B2 | 3/2010 | Menkedick et al. |
| 7,676,866 B2 | 3/2010 | Toms et al. |
| 7,679,520 B2 | 3/2010 | Zerhusen et al. |
| 7,690,059 B2 | 4/2010 | Lemire et al. |
| 7,703,158 B2 | 4/2010 | Wilker, Jr. et al. |
| 7,716,762 B2 | 5/2010 | Ferraresi et al. |
| 7,746,218 B2 | 6/2010 | Collins, Jr. et al. |
| 7,761,942 B2 | 7/2010 | Benzo et al. |
| 7,779,493 B2 | 8/2010 | Lemire et al. |
| 7,805,784 B2 | 10/2010 | Lemire et al. |
| 7,834,768 B2 | 11/2010 | Dixon et al. |
| 7,836,531 B2 | 11/2010 | Girard et al. |
| 7,861,334 B2 | 1/2011 | Lemire et al. |
| 7,874,695 B2 | 1/2011 | Jensen |
| 7,962,981 B2 | 6/2011 | Lemire et al. |
| 7,978,084 B2 | 7/2011 | Dixon et al. |
| 8,051,513 B2 | 11/2011 | Reed et al. |
| 8,117,701 B2 | 2/2012 | Bobey et al. |
| 8,416,084 B2 | 4/2013 | Beltmann et al. |
| 8,537,008 B2 | 9/2013 | Tallent et al. |
| 8,593,284 B2 | 11/2013 | Tallent et al. |
| 8,878,679 B2 | 11/2014 | Arndt et al. |
| 9,827,156 B2 | 11/2017 | Zerhusen |
| 2001/0011393 A1 | 8/2001 | Brooke et al. |
| 2001/0032362 A1 | 10/2001 | Welling et al. |
| 2002/0002742 A1 | 1/2002 | Osborne et al. |
| 2002/0044059 A1 | 4/2002 | Reeder et al. |
| 2002/0066142 A1 | 6/2002 | Osborne et al. |
| 2002/0138902 A1 | 10/2002 | Bennett |
| 2002/0151990 A1 | 10/2002 | Ulrich et al. |
| 2003/0052787 A1 | 3/2003 | Zerhusen et al. |
| 2003/0061664 A1 | 4/2003 | Salvatini et al. |
| 2003/0197614 A1 | 10/2003 | Smith et al. |
| 2004/0034936 A1 | 2/2004 | Welling et al. |
| 2004/0103475 A1 | 6/2004 | Ogawa et al. |
| 2004/0122476 A1 | 6/2004 | Wung |
| 2004/0128765 A1 | 7/2004 | Osborne et al. |
| 2004/0130452 A1 | 7/2004 | Cherubini |
| 2004/0177443 A1 | 9/2004 | Simmonds et al. |
| 2004/0177445 A1 | 9/2004 | Osborne et al. |
| 2004/0227737 A1 | 11/2004 | Novak et al. |
| 2005/0035871 A1 | 2/2005 | Dixon et al. |
| 2005/0137530 A1 | 6/2005 | Campbell et al. |
| 2005/0165325 A1 | 7/2005 | Hornig |
| 2005/0166324 A1 | 8/2005 | Dixon et al. |
| 2005/0172405 A1 | 8/2005 | Menkedick et al. |
| 2005/0187463 A1 | 8/2005 | Quistgaard et al. |
| 2005/0188462 A1 | 9/2005 | Heimbrock |
| 2005/0219059 A1 | 10/2005 | Ulrich et al. |
| 2006/0049936 A1 | 3/2006 | Collins et al. |
| 2006/0053555 A1 | 3/2006 | Poulos et al. |
| 2006/0075560 A1 | 4/2006 | Osborne et al. |
| 2006/0096029 A1 | 5/2006 | Osborne et al. |
| 2006/0097879 A1 | 5/2006 | Lippincott |
| 2006/0101581 A1 | 5/2006 | Blanchard et al. |
| 2006/0117482 A1 | 6/2006 | Branson |
| 2006/0162079 A1 | 7/2006 | Menkedick et al. |
| 2006/0168730 A1 | 8/2006 | Menkedick et al. |
| 2006/0168731 A1 | 8/2006 | Menkedick et al. |
| 2006/0271207 A1 | 11/2006 | Shaw |
| 2006/0277683 A1 | 12/2006 | Lamire et al. |
| 2007/0076852 A1 | 4/2007 | Ishikawa et al. |
| 2007/0130692 A1 | 6/2007 | Lemire et al. |
| 2007/0156031 A1 | 7/2007 | Sullivan et al. |
| 2007/0157385 A1 | 7/2007 | Lemire et al. |
| 2007/0163043 A1 | 7/2007 | Lemire et al. |
| 2007/0163045 A1 | 7/2007 | Becker et al. |
| 2007/0164871 A1 | 7/2007 | Dionne et al. |
| 2007/0169268 A1 | 7/2007 | Lemire et al. |
| 2007/0174964 A1 | 8/2007 | Lemire et al. |
| 2007/0174965 A1 | 8/2007 | Lemire et al. |
| 2007/0180616 A1 | 8/2007 | Newkirk et al. |
| 2007/0210917 A1 | 9/2007 | Collins et al. |
| 2007/0268480 A1 | 11/2007 | Kaye |
| 2008/0005838 A1 | 1/2008 | Wan Fong et al. |
| 2008/0010747 A1 | 1/2008 | Dixon et al. |
| 2008/0010748 A1 | 1/2008 | Menkedick et al. |
| 2008/0169931 A1 | 7/2008 | Gentry et al. |
| 2008/0172789 A1 | 7/2008 | Elliot et al. |
| 2008/0201847 A1 | 8/2008 | Menkedick et al. |
| 2008/0201851 A1 | 8/2008 | Menkedick et al. |
| 2008/0205311 A1 | 8/2008 | Perkins et al. |
| 2008/0235872 A1 | 10/2008 | Newkirk et al. |
| 2008/0289108 A1 | 11/2008 | Menkedick et al. |
| 2009/0031498 A1 | 2/2009 | Girard et al. |
| 2009/0089930 A1 | 4/2009 | Benzo et al. |
| 2009/0094744 A1 | 4/2009 | Benzo et al. |
| 2009/0094745 A1 | 4/2009 | Benzo et al. |
| 2009/0094746 A1 | 4/2009 | Ferraresi et al. |
| 2009/0237264 A1 | 9/2009 | Bobey et al. |

(56) References Cited

U.S. PATENT DOCUMENTS

| | | |
|---|---|---|
| 2009/0302782 A1 | 12/2009 | Smith |
| 2009/0313758 A1 | 12/2009 | Menkedick et al. |
| 2010/0000018 A1 | 1/2010 | Eleonori et al. |
| 2010/0052917 A1 | 3/2010 | Sullivan et al. |
| 2010/0073168 A1 | 3/2010 | Tallent et al. |
| 2010/0275376 A1 | 11/2010 | Benzo et al. |
| 2010/0287703 A1 | 11/2010 | Zapata |
| 2011/0010854 A1 | 1/2011 | Zerhusen et al. |
| 2011/0037597 A1 | 2/2011 | Dixon et al. |
| 2011/0119940 A1 | 5/2011 | Zerhusen |
| 2011/0133935 A1 | 6/2011 | Beltmann et al. |
| 2011/0157486 A1 | 6/2011 | Murata et al. |
| 2011/0162141 A1 | 7/2011 | Lemire et al. |
| 2011/0169653 A1 | 7/2011 | Wang et al. |
| 2011/0231996 A1 | 9/2011 | Lemire et al. |
| 2011/0234411 A1 | 9/2011 | Harrington et al. |
| 2011/0277242 A1 | 11/2011 | Dionne et al. |
| 2012/0046100 A1 | 2/2012 | Romn et al. |
| 2012/0105233 A1 | 5/2012 | Bobey et al. |
| 2012/0194356 A1 | 8/2012 | Haines et al. |
| 2014/0292529 A1 | 10/2014 | Zerhusen |

FOREIGN PATENT DOCUMENTS

| | | |
|---|---|---|
| EP | 1354539 A1 | 10/2003 |
| EP | 1477110 A1 | 11/2004 |
| JP | 02141447 A | 5/1990 |
| JP | 02156950 A | 6/1990 |
| JP | 03047860 A | 2/1991 |
| JP | 07107195 A | 4/1995 |
| JP | 11290395 A | 10/1999 |
| JP | 11299837 A | 11/1999 |
| JP | 2003164496 A | 6/2003 |
| JP | 2003524483 A | 8/2003 |
| JP | 2004049706 A | 2/2004 |
| JP | 2004141484 A | 5/2004 |
| JP | 2005118147 A | 5/2005 |
| JP | 2005168913 A | 6/2005 |
| JP | 2005185346 A | 7/2005 |
| WO | 9720534 A1 | 6/1997 |
| WO | 0147340 A2 | 7/2001 |
| WO | 0175834 A1 | 10/2001 |
| WO | 0185058 A2 | 11/2001 |
| WO | 2004093023 A2 | 10/2004 |
| WO | 2007056342 A2 | 5/2007 |
| WO | 2013053040 A1 | 4/2013 |
| WO | 2013071246 A1 | 5/2013 |

OTHER PUBLICATIONS

Hill-Rom "ProAxis Plus Bed User Manual—13867(5)", 2005.
European Search Report on EP Application No. EP 14 15 9531, dated Jun. 25, 2014, 4 pages.
Centra From Hill-Rom. Hill-Rom 1992.
In Services Manual Centra Bed from Hill-Rom, Hill-Rom 1996.
The Advance 2000 Bed from Hill-Rom, Hill-Rom 1993.
Adel 500XL Childbearing Bed, Stryker Patient Care, May 1995.
Stryker Adel 2100EC Childbearing Bed, Stryker Patient care, Jan. 1994.
Advantage Stretcher Stryker Patient Handling, May 1994.
Hausted Gemini Series, Hausted, Inc., Oct. 1993.
Silenzio, Silenzio Plus, Silenzio, Delta, Nasal CPAP System, Operator's Guide, Jun. 2003.
Gaymar, Aire Twin, Alternating Pressure and Low-Air-Loss Therapy Mattress Replacement Systems, Operator's Manual, 2005.
Hill-Rom, User Manual, TotalCare Bariatric Bed, Product No. P1830A, Apr. 2003.

BED EXIT ALERTS FOR PERSON SUPPORT APPARATUS

CROSS REFERENCE TO RELATED APPLICATIONS

This application is a continuation of U.S. application Ser. No. 14/356,041, filed May 2, 2014, which is the U.S. National Phase application under 35 U.S.C. § 371 of International Application No. PCT/US12/64692, filed Nov. 12, 2012, which claims the benefit of U.S. Provisional Application No. 61/559,035, filed Nov. 11, 2011, and each of which is incorporated herein by reference.

BACKGROUND OF THE DISCLOSURE

This disclosure relates particularly, but not exclusively, to person support apparatuses. While various person support apparatuses have been developed, there is still room for improvement. Thus a need persists for further contributions in this area of technology.

SUMMARY OF THE DISCLOSURE

In one illustrative embodiment, a mattress includes hinged extensions along the sides of the mattress that are moved from a nested position to the extension position. In another illustrative embodiment, the pendant includes a plurality of screen keys that can be pressed to cycle through various control modes for the person support apparatus. In another illustrative embodiment, a night light system can be configured to display a message or image on the floor communicating information to the person and/or alerting the person as to when they are able to exit the bed.

Additional features alone or in combination with any other feature(s), including those listed above and those listed in the claims and those described in detail below, can comprise patentable subject matter. Others will become apparent to those skilled in the art upon consideration of the following detailed description of illustrative embodiments exemplifying the best mode of carrying out the invention as presently perceived.

BRIEF DESCRIPTION OF THE DRAWINGS

Referring now to the illustrative examples in the drawings, wherein like numerals represent the same or similar elements throughout.

DETAILED DESCRIPTION OF THE DRAWINGS

Figure 1:
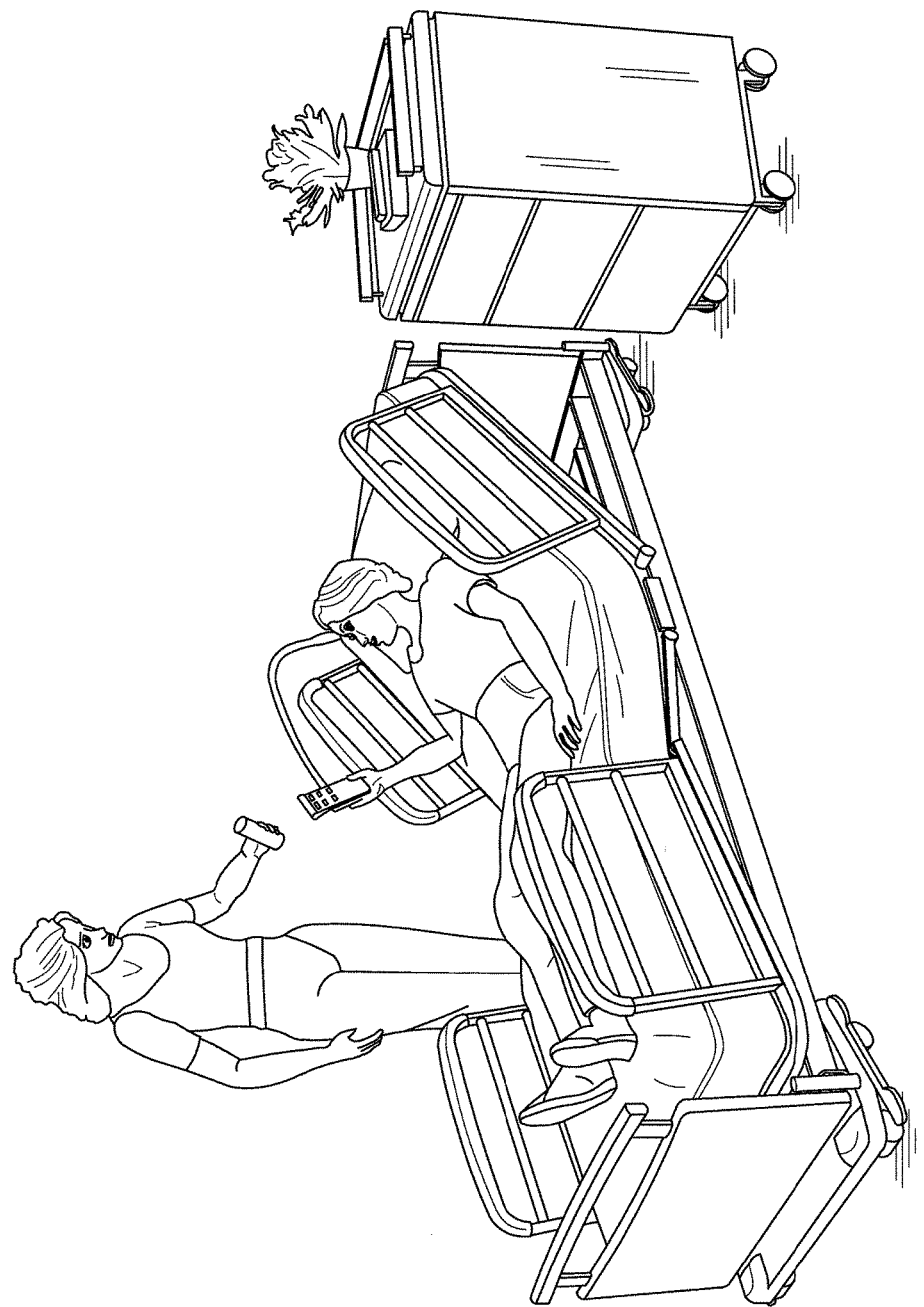
FIG. 1 is a person support apparatus according to one contemplated embodiment of the current disclosure showing the upper frame in a in a low reclined position with a pendant holder attached to the head section.

While the present disclosure can take many different forms, for the purpose of promoting an understanding of the principles of the disclosure, reference will now be made to the embodiments illustrated in the drawings, and specific language will be used to describe the same. No limitation of the scope of the disclosure is thereby intended. Various alterations, further modifications of the described embodiments, and any further applications of the principles of the disclosure, as described herein, are contemplated.

A person support apparatus 10 according to one illustrative embodiment of the current disclosure is shown in FIGS. 1-47. The person support apparatus 10 is a hospital bed with a first section F1 or head support section F1, where the head of a person (not shown) can be positioned and a second section S1 or a foot support section S1, where the feet of the person (not shown) can be positioned. In other contemplated embodiments, the person support apparatus 10 can be a hospital stretcher, an operating table, a wheelchair, or other apparatus configured to support a person.

Figure 2:
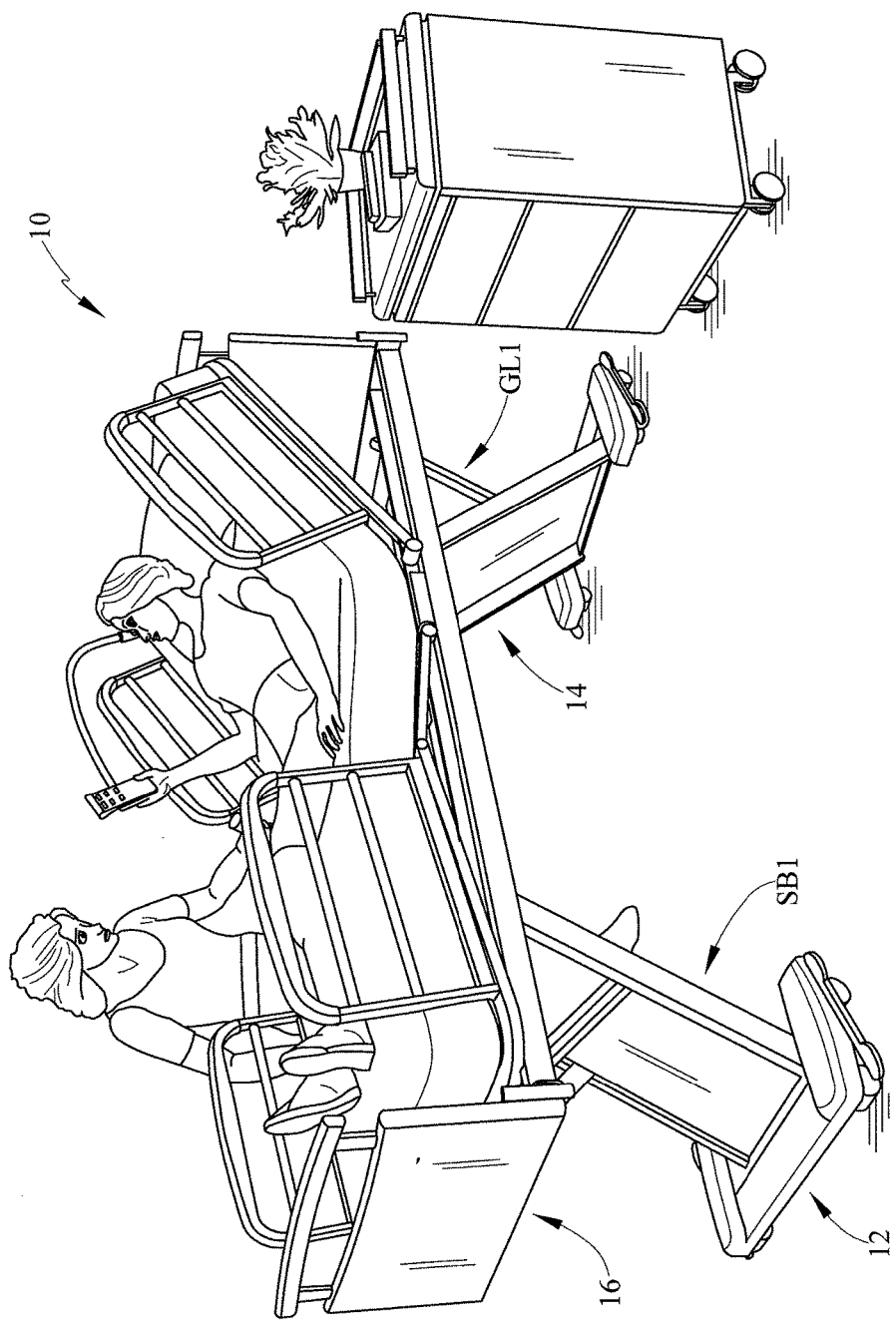
FIG. 2 is the person support apparatus of FIG. 1 with the upper frame in a raised position.

The person support apparatus 10 includes a lower frame 12 or base 12, a plurality of supports 14 coupled to the lower frame 12 and an upper frame 16 movably supported by the plurality of supports 14 above the lower frame 12 as shown in FIG. 2. In one illustrative embodiment, the supports 14 are lift mechanisms 14 that move the upper frame 16 with respect to the lower frame 12. In another illustrative embodiment, the lift mechanisms 14 cooperate with the lower frame to raise and lower the upper frame. In some contemplated embodiments, the supports 14 employ a Evans-link system where the support beam SB1 is pivotably coupled to the lower frame 12 and slidably coupled to the upper frame 16, a guide link GL1 is pivotably coupled to the upper frame 16 and the support beam SB1, and a linear actuator (not shown) engages the support beam SB1 to raise/lower the person support apparatus 10.

Figure 3:
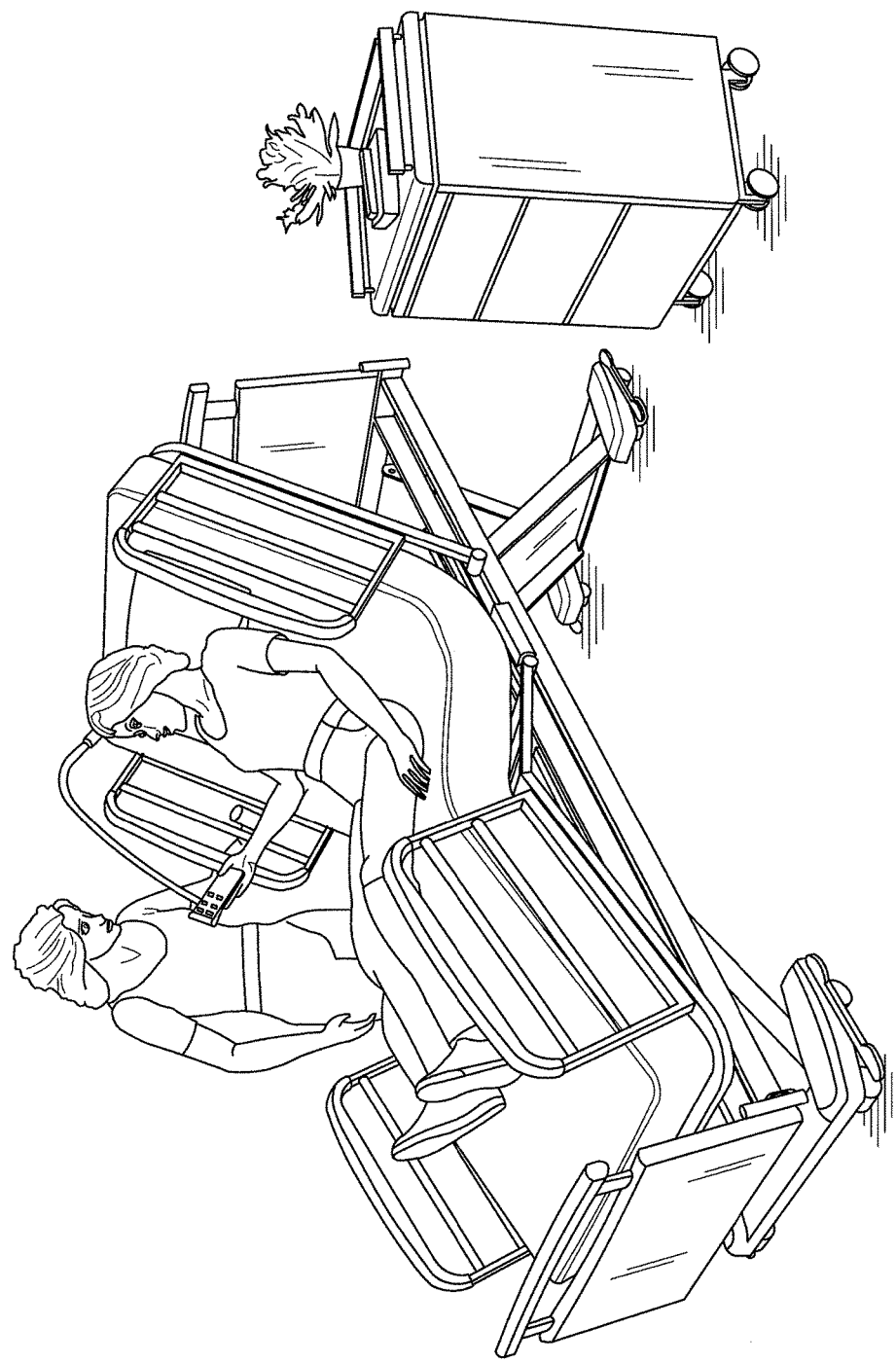
FIG. 3 is the person support apparatus of FIG. 1 in the reclined, reverse-Trendelenburg position.
Figure 4:
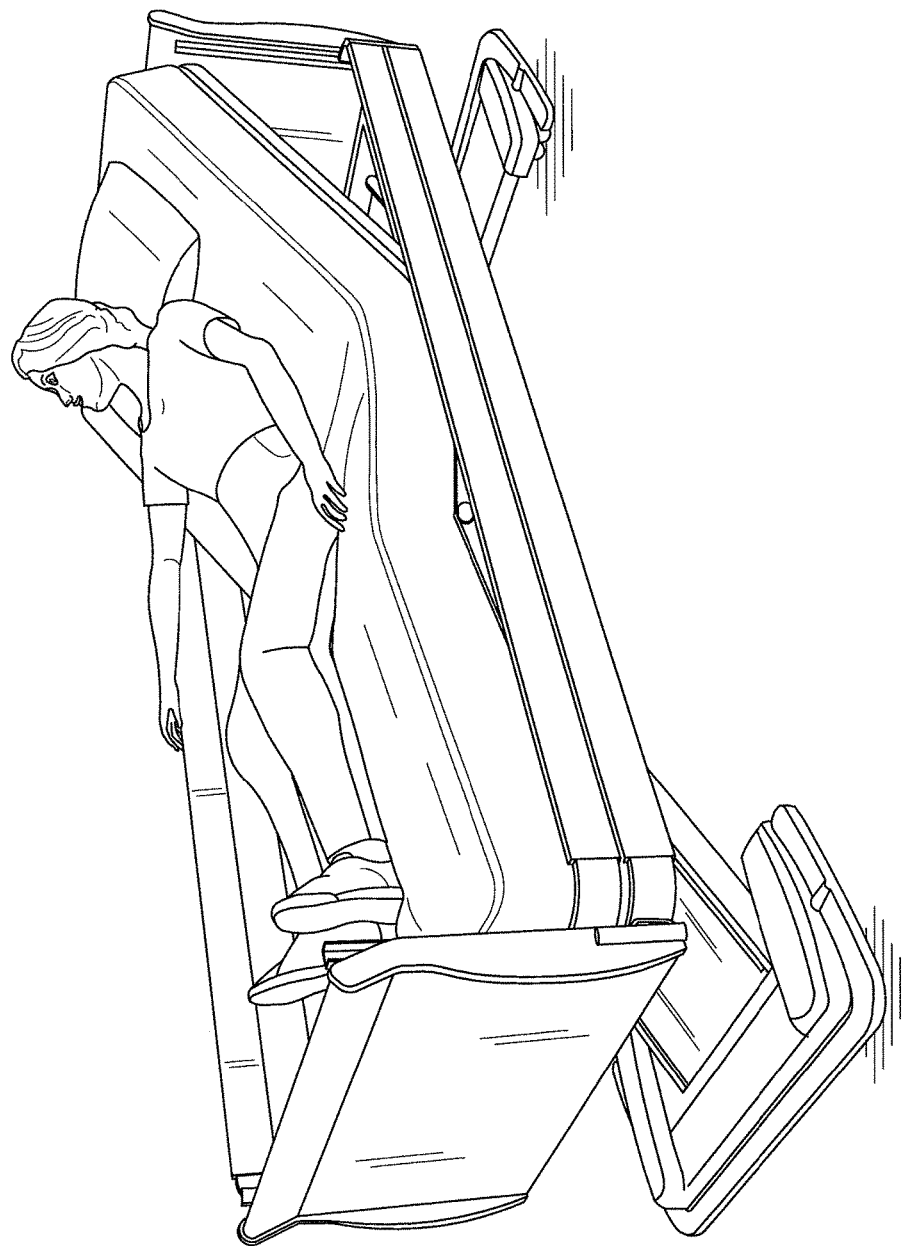
FIG. 4 is a person support apparatus according to another contemplated embodiment of the current disclosure showing a full length siderail coupled to the upper frame.
Figure 30:
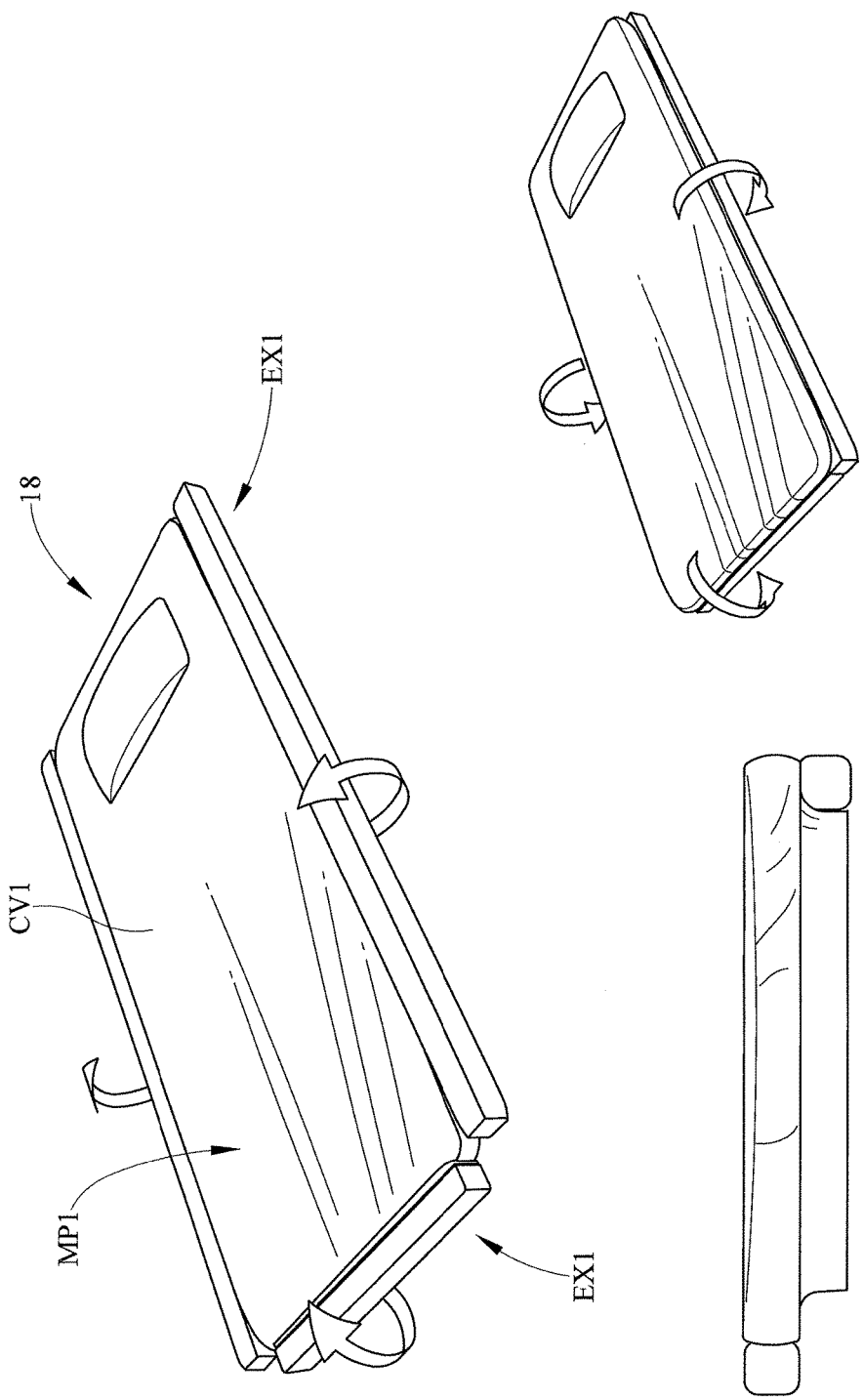
FIG. 30 is the mattress of FIG. 29 showing a main portion with extensions pivotably coupled there to that are configured to move between a nested position and an extended position.
Figure 31:
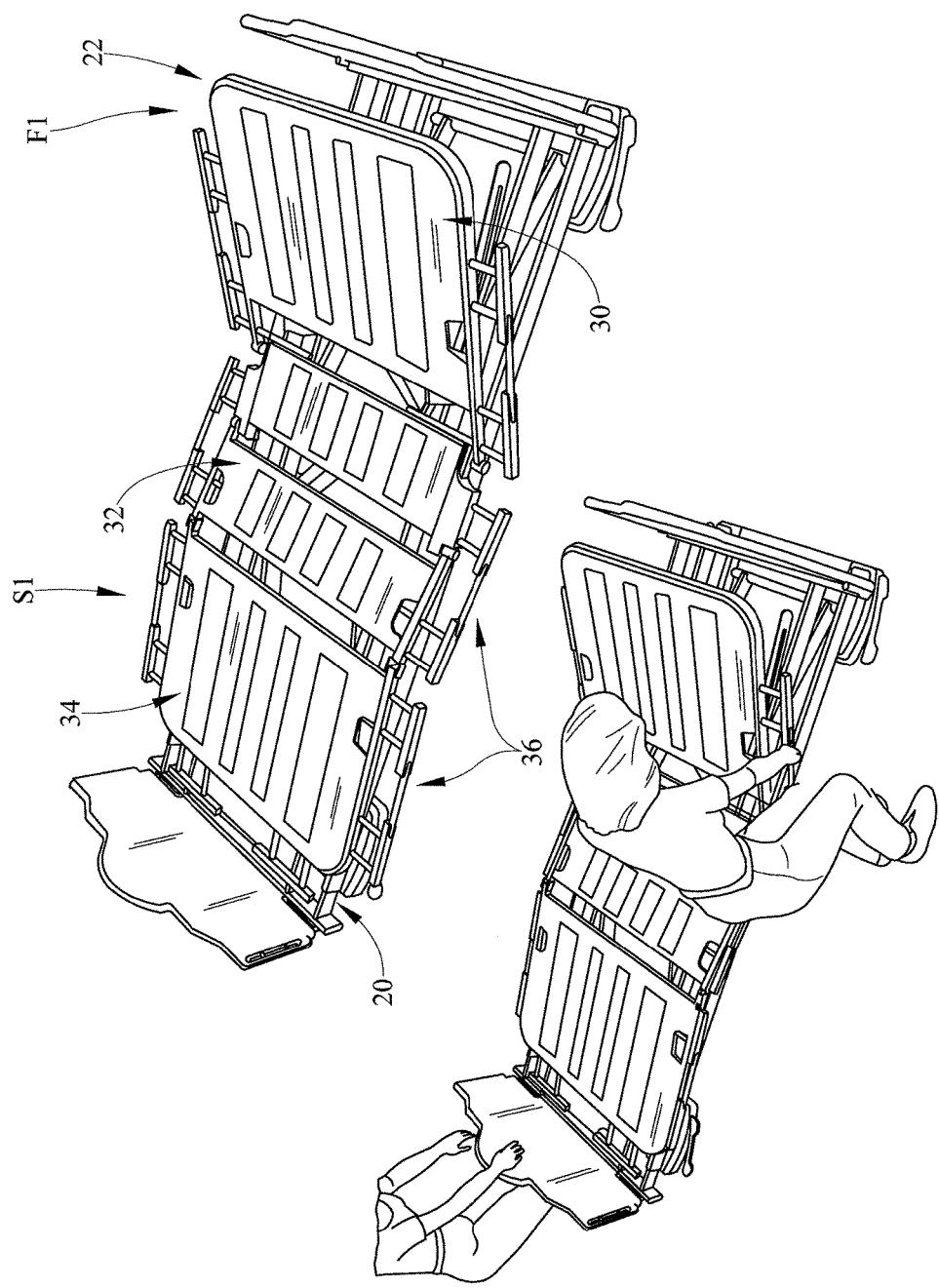
FIG. 31 is a person support apparatus according to another contemplated embodiment of the current disclosure showing the frame width and length extensions.
Figure 32:
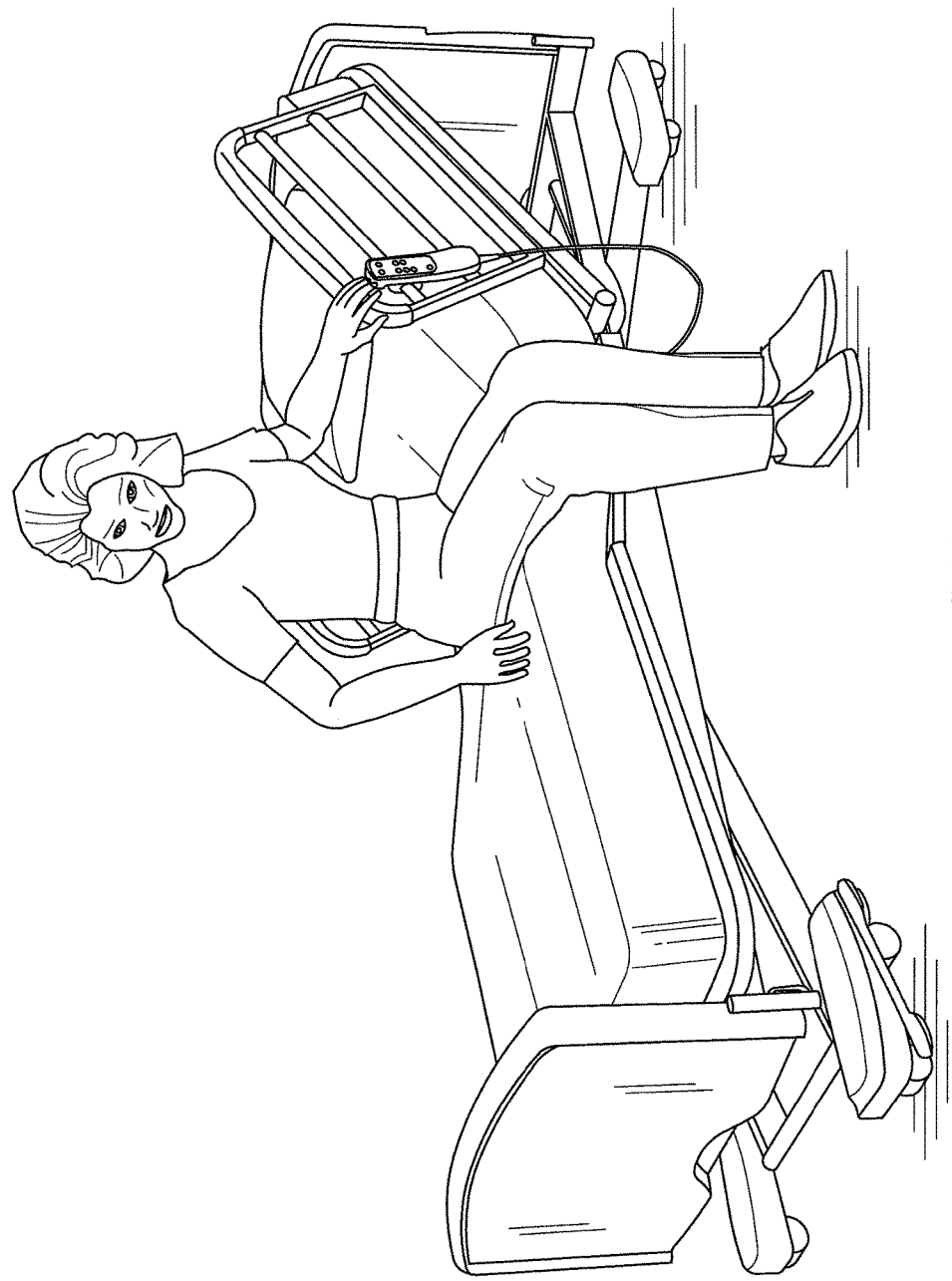
FIG. 32 is a person support apparatus according to another contemplated embodiment of the current disclosure.
Figure 33:
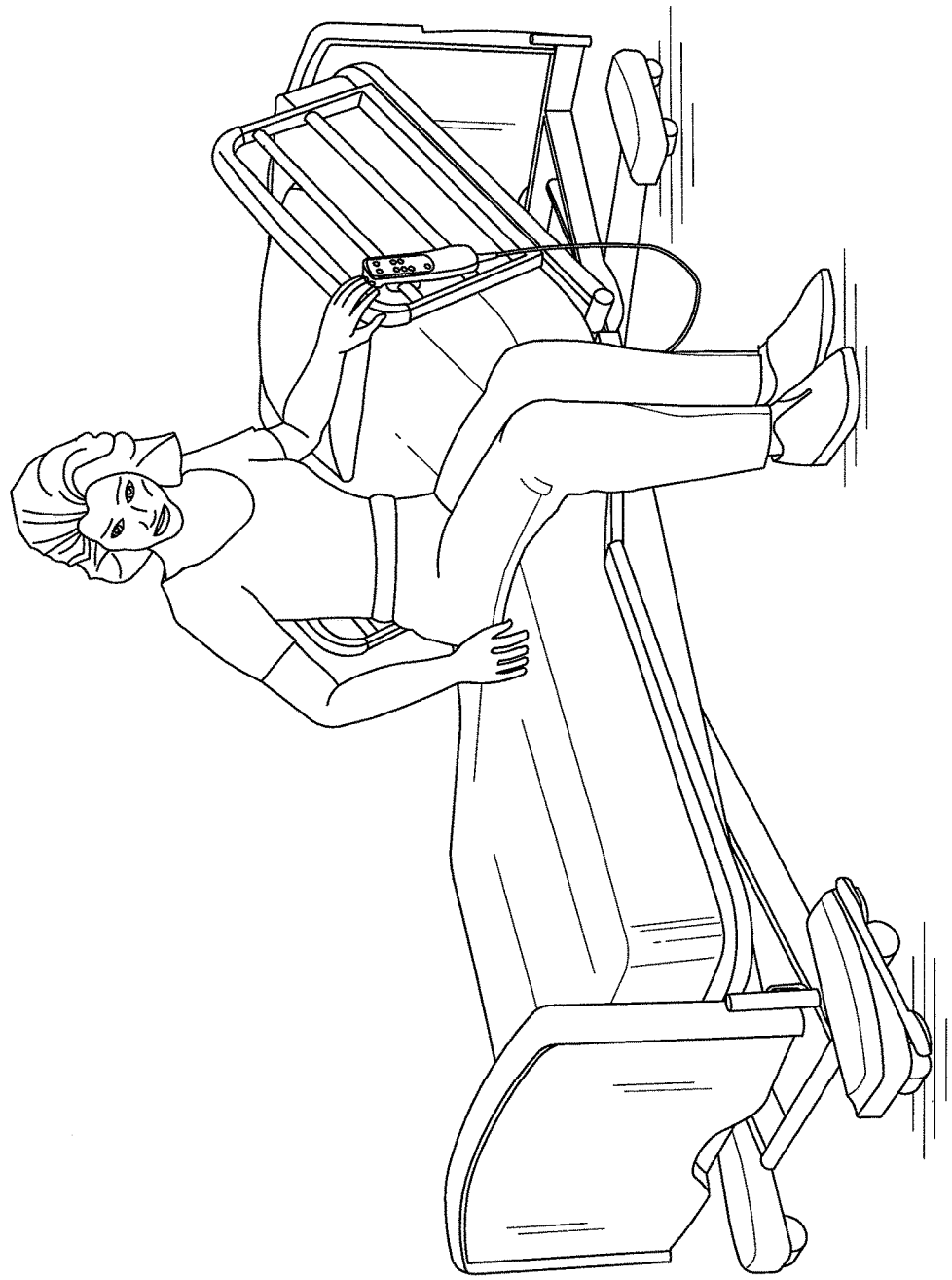
FIG. 33 is a person support apparatus according to another contemplated embodiment of the current disclosure.
Figure 34:
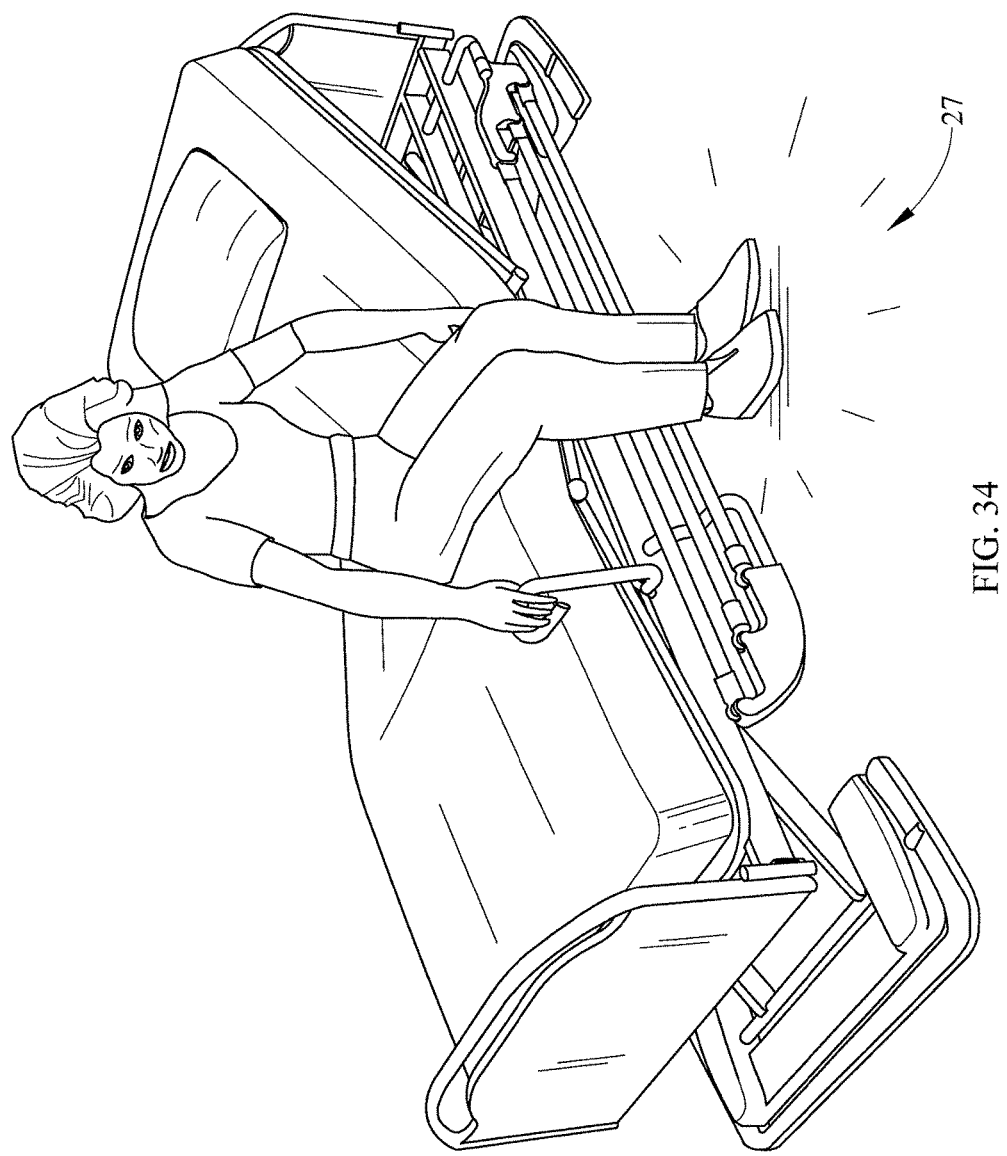
FIG. 34 is a person support apparatus according to another contemplated embodiment of the current disclosure showing a night-light configured to alert the user to a status of the person support apparatus, such as, when the person support apparatus is in a position where the occupant can egress from the bed. The light illuminating the floor with a red light to indicate that the user of an unsatisfactory condition, such as, that the bed is not in a predetermined egress position.
Figure 35:
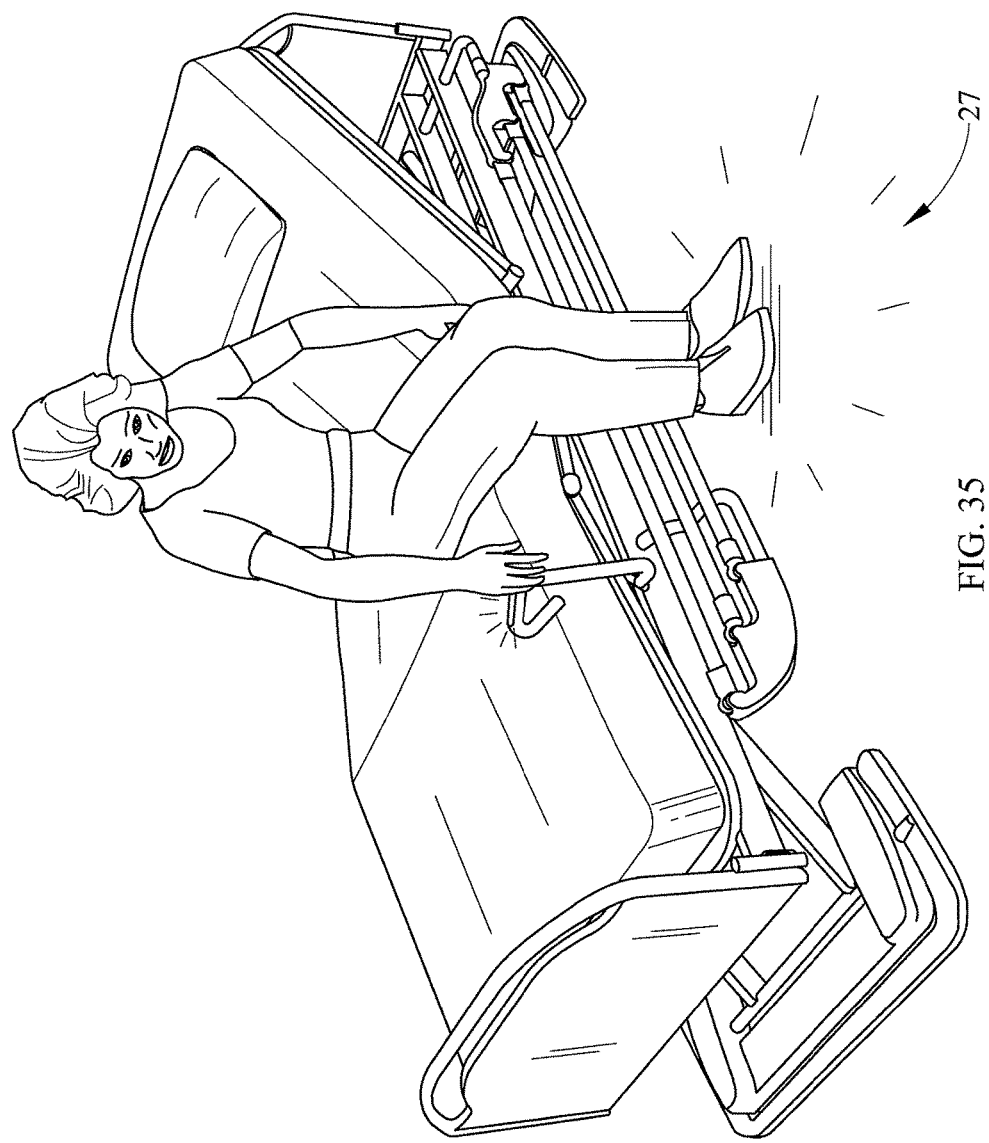
FIG. 35 is the person support apparatus of FIG. 34, wherein the handle of the grip and the floor are illuminated with a green light to indicate that the occupant can egress from the bed.

The upper frame 16 includes an upper frame base 20, a deck 22, siderails 24, endboards 26 (including a head endboard 26a and a foot endboard 26b), a control system CS1, a night light 27, and a pendant 28 as shown in FIGS. 1-47. The upper frame base 20 is coupled to the supports 14 and supports the deck 22, the siderails 24, and the endboards 26. The deck 22 includes a head portion 30, a seat portion 32, and a foot portion 34 as shown in FIGS. 1-2. The head portion 30, the seat portion 32, and the foot portion 34 are movably coupled to each other and the upper frame base 20 and are configured to cooperate with one another to move the deck 22 between a relatively horizontal position and a chair position as shown in FIG. 3. In other contemplated embodiments, the deck 22 is configured to move between a relatively horizontal position and a reclined position. The deck 22 includes deck extensions 36 that are configured to slide out from the sides of the portions of the deck 22 to increase the width of the deck 22 as shown in FIG. 31.

Figure 5:
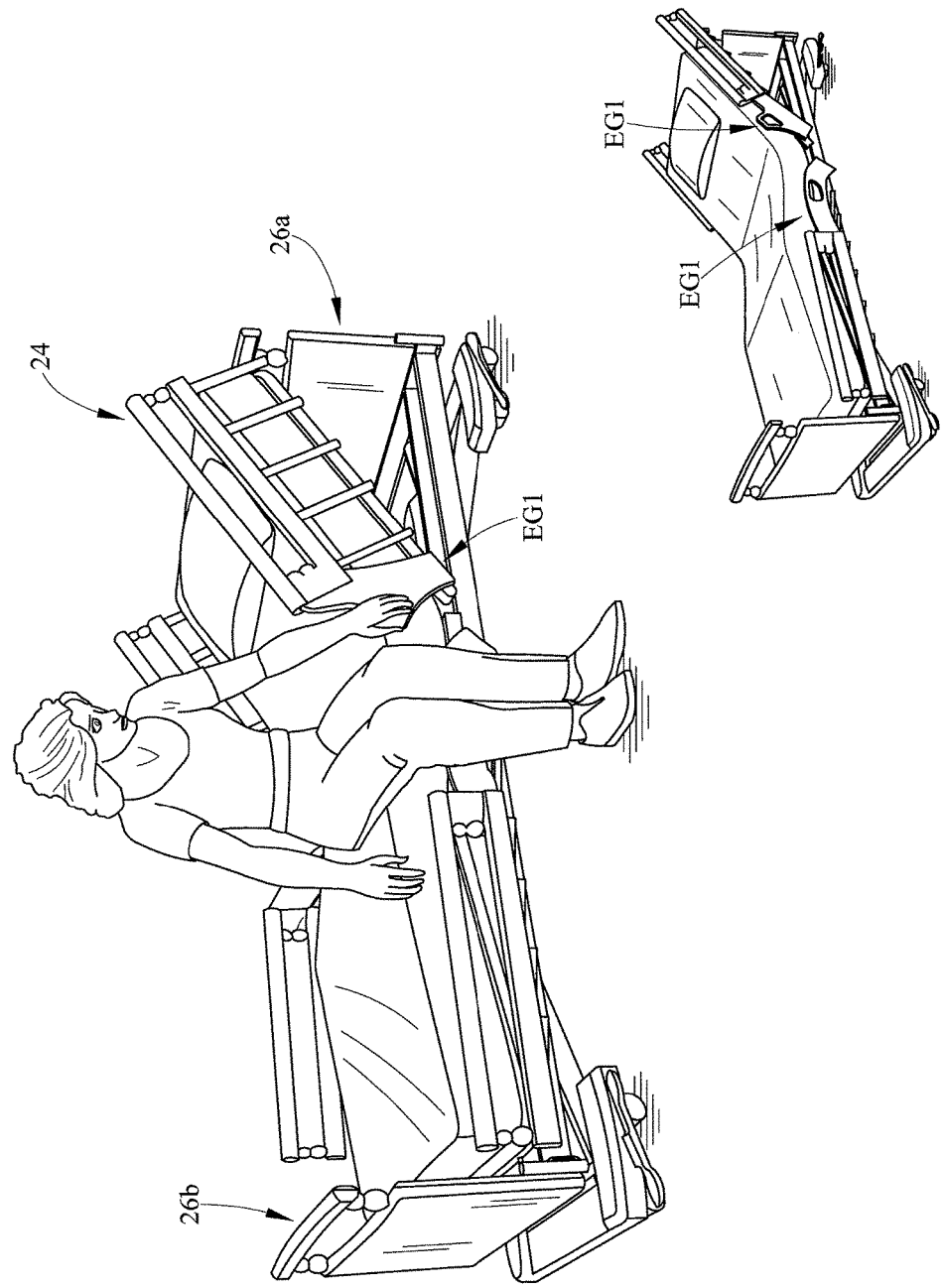
FIG. 5 is a person support apparatus according to another contemplated embodiment of the current disclosure showing a collapsible siderail with an egress grip integrated into the siderail movement mechanism.
Figure 6:
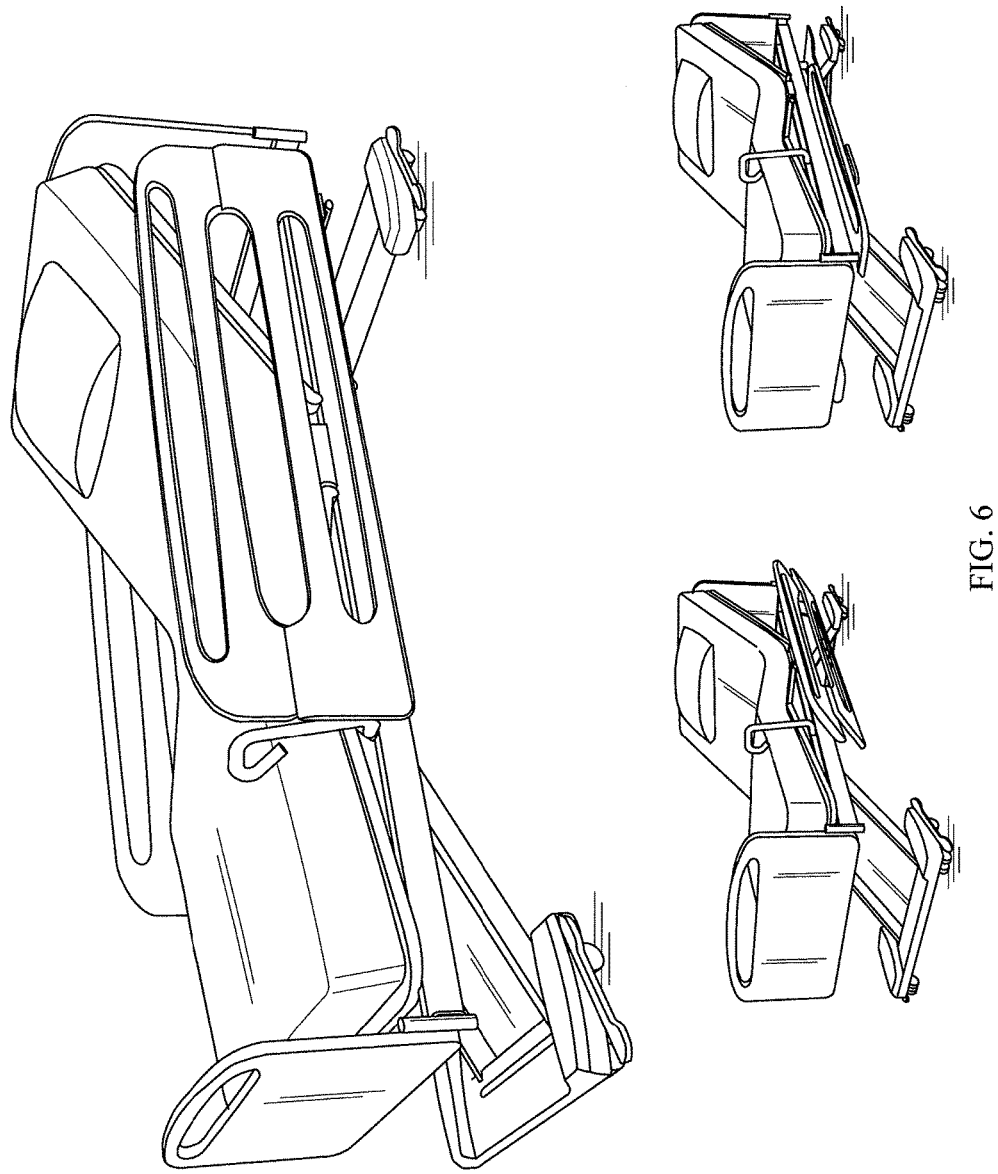
FIG. 6 is a person support apparatus according to another contemplated embodiment of the current disclosure showing an egress grip coupled to the upper frame and a foldable siderail configured to be rotated and stowed beneath the upper frame.
Figure 7:
FIG. 7 is a person support apparatus according to another contemplated embodiment of the current disclosure showing the egress grip of FIG. 6 and a collapsible, clocking siderail coupled to the upper frame.
Figure 8:
FIG. 8 is a person support apparatus according to another contemplated embodiment of the current disclosure.
Figure 9:
FIG. 9 is the person support apparatus of FIG. 8 with the foot end siderails removed.
Figure 10:
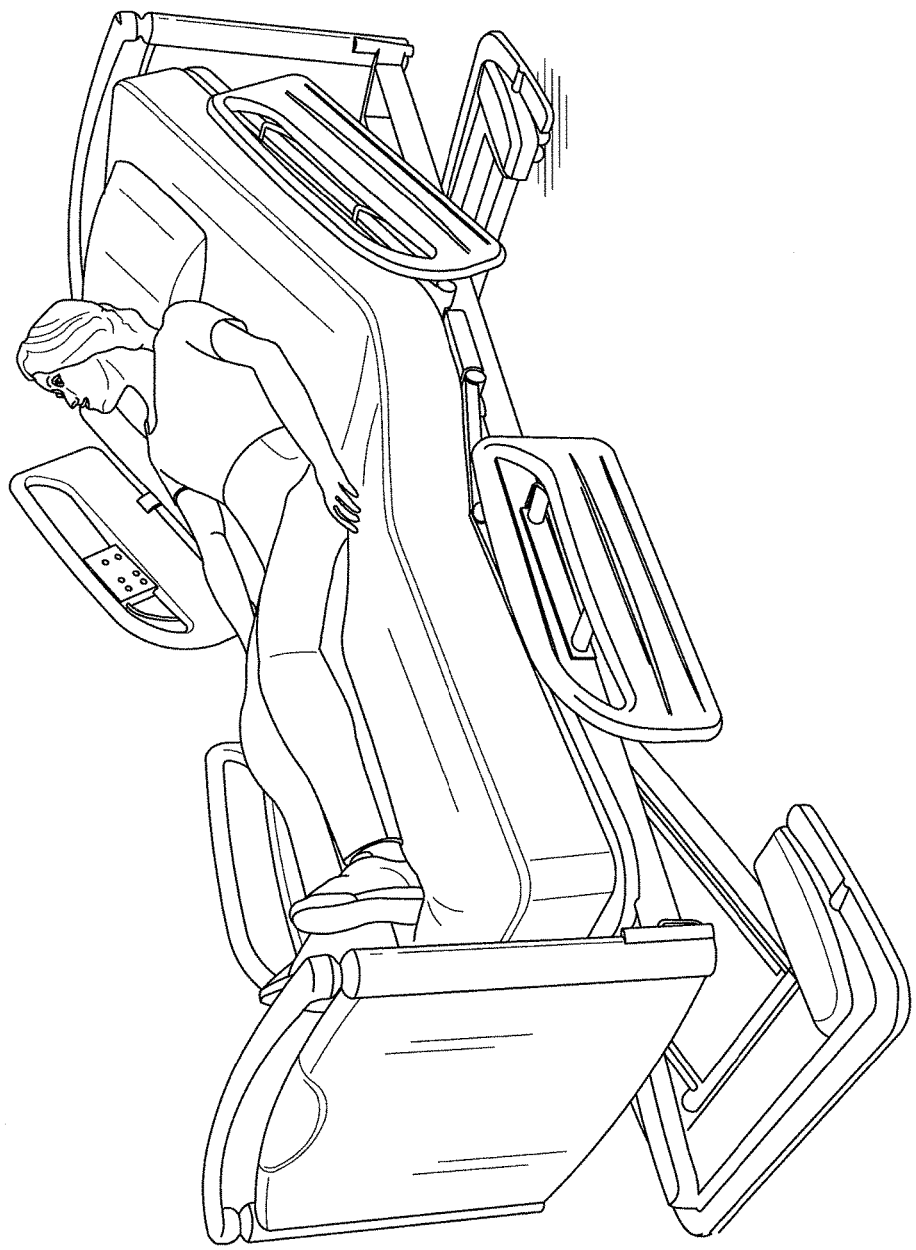
FIG. 10 is a person support apparatus according to another contemplated embodiment of the current disclosure.
Figure 11:
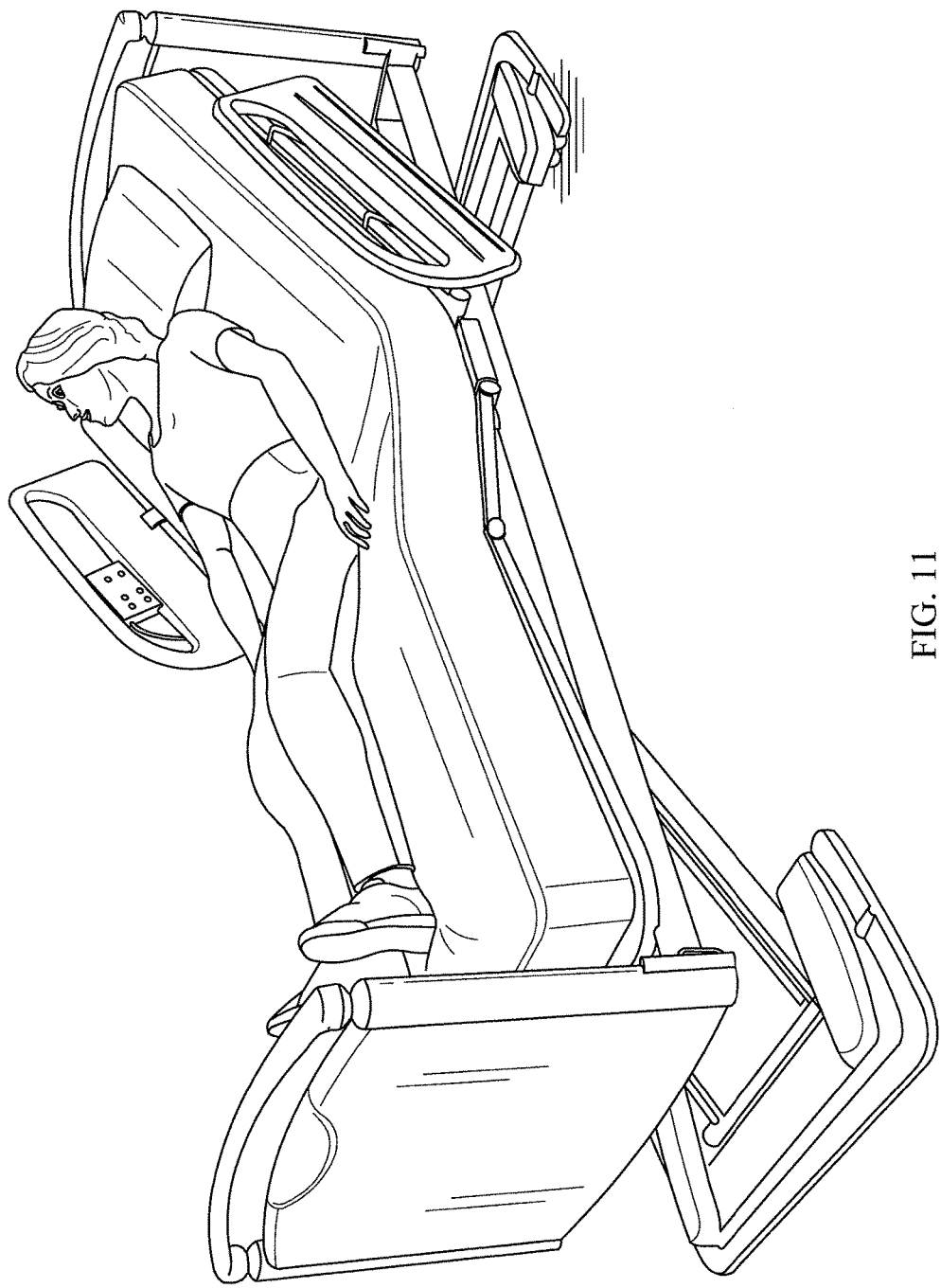
FIG. 11 is the person support apparatus of FIG. 9 with the foot end siderails removed.
Figure 12:
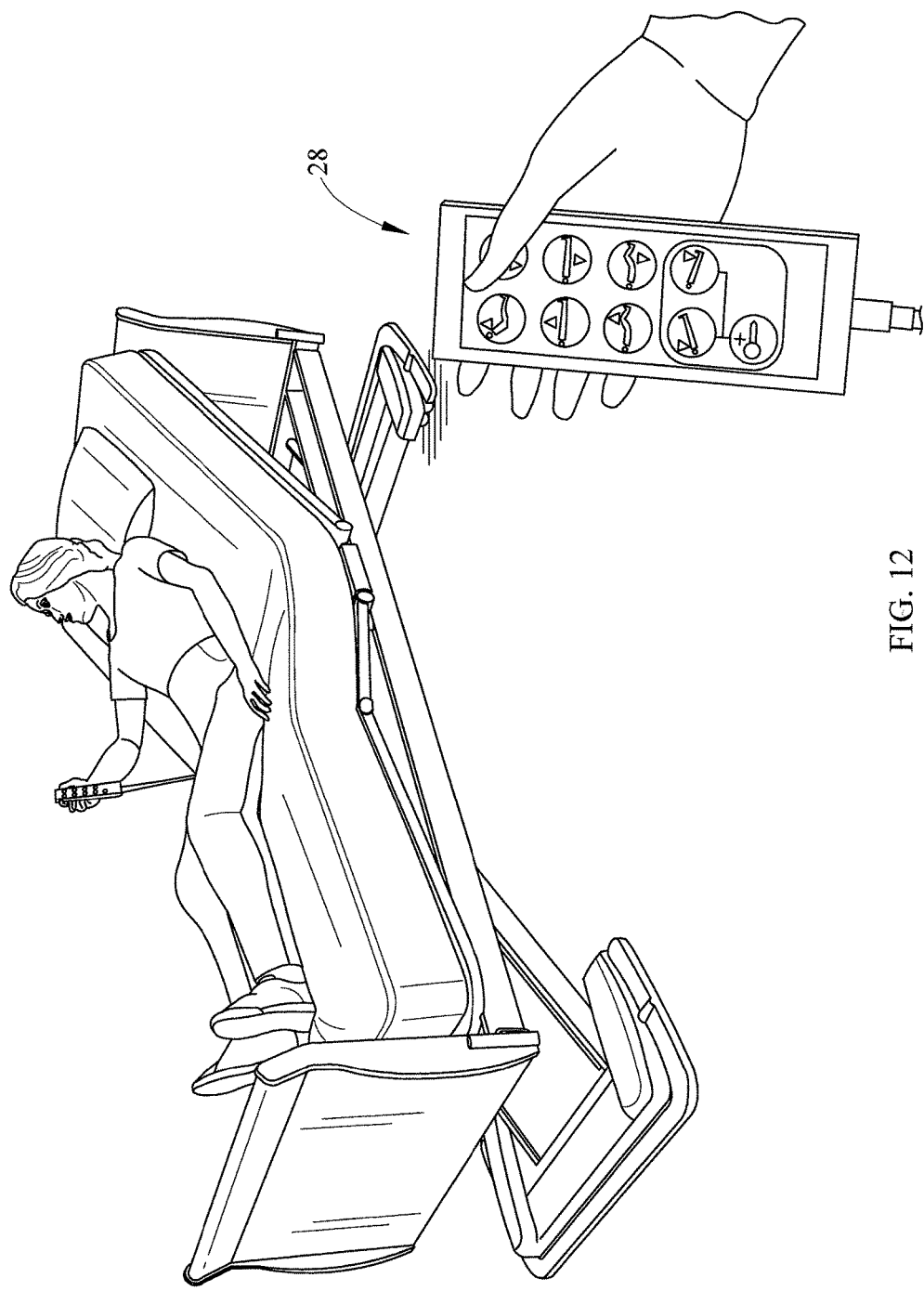
FIG. 12 is a person support apparatus according to another contemplated embodiment of the current disclosure showing a pendant and brake-steer pedals coupled to the lower frame.
Figure 13:
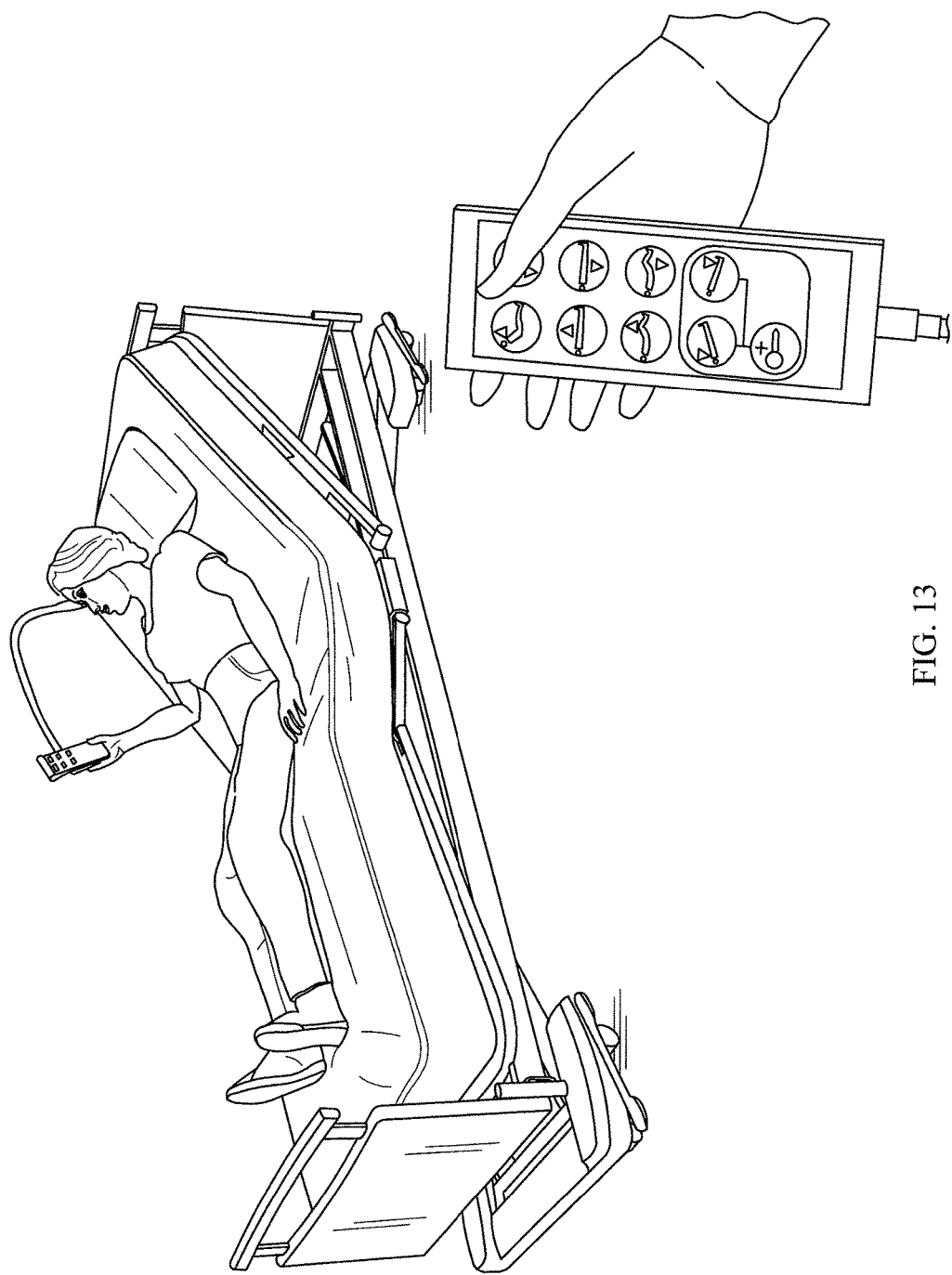
FIG. 13 is a person support apparatus according to another contemplated embodiment of the current disclosure showing a pendant holder coupled to the head end of the person support apparatus.
Figure 14:
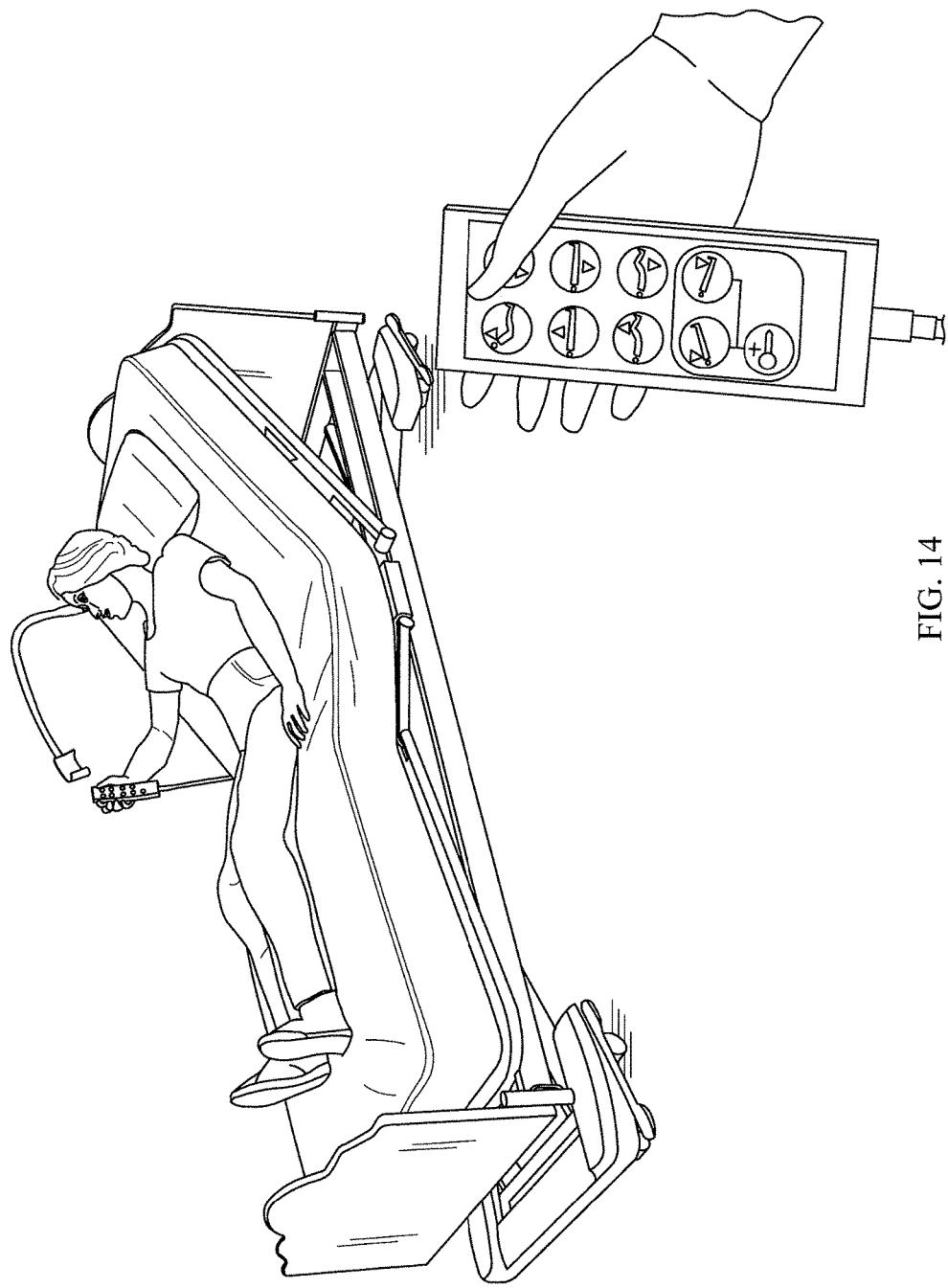
FIG. 14 is a person support apparatus of FIG. 13 according to another contemplated embodiment of the current disclosure.
Figure 15:
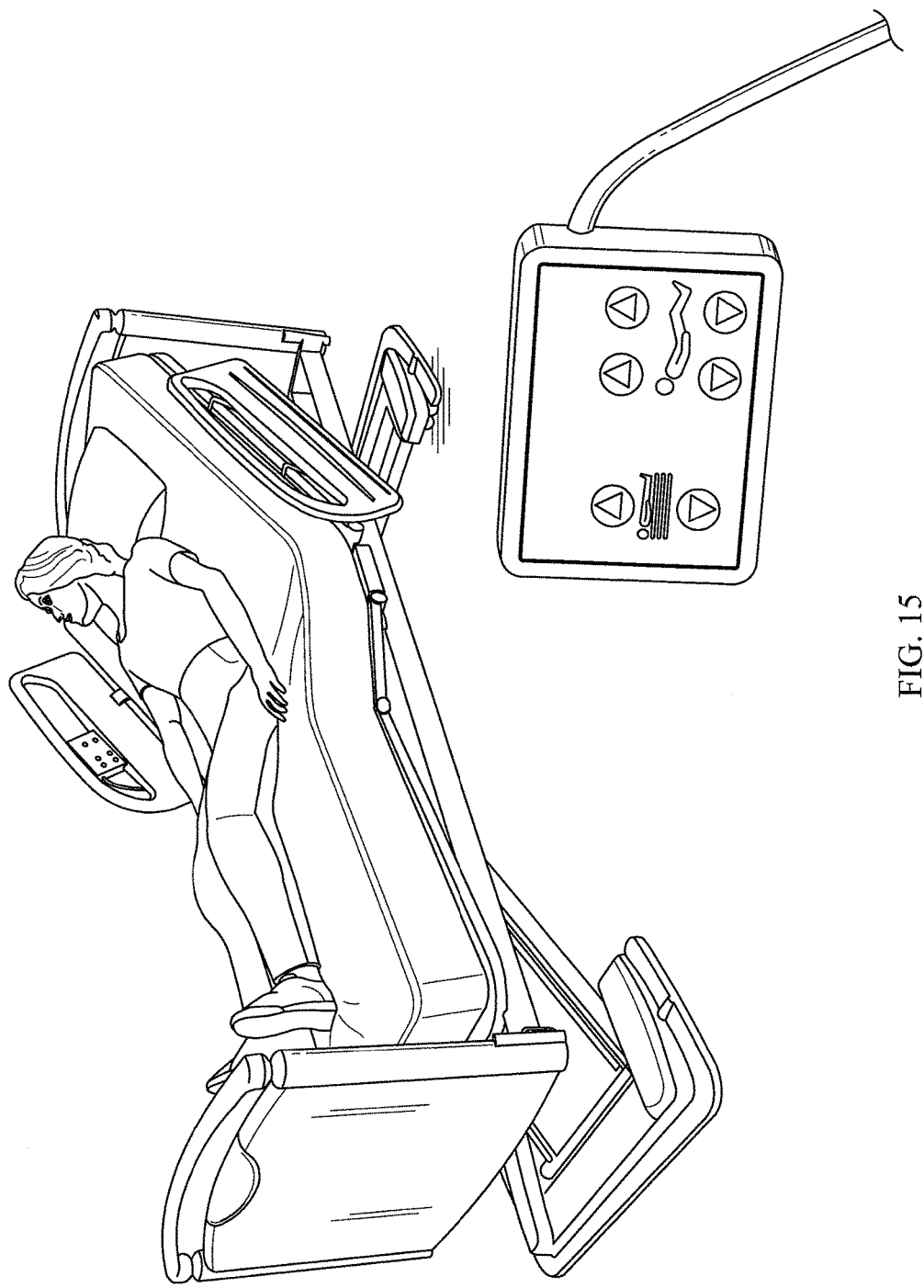
FIG. 15 is a person support apparatus according to another contemplated embodiment of the current disclosure showing a pendant coupled within the siderail grip opening of a siderail.
Figure 16:
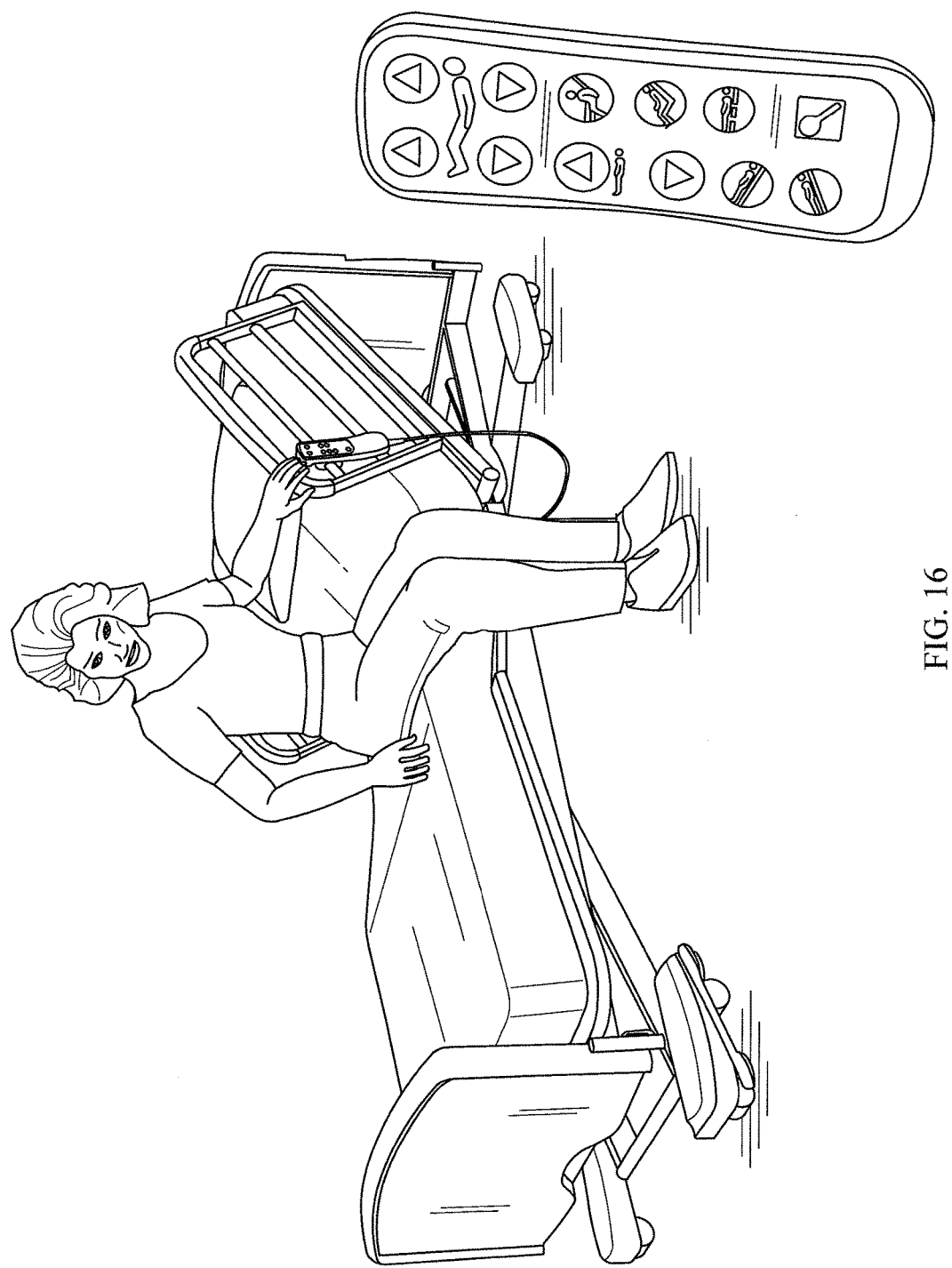
FIG. 16 is a pendant according to another illustrative embodiment of the current disclosure.

The siderails 24 include hingedly coupled to the upper frame 16 and are configured to rotate from a raised position to a collapsed storage position as shown in FIG. 5. The siderails 24 include an egress grip portion EG1 configured to provide assistance to a person egressing/ingressing to/from the person support apparatus 10. The adjacent egress grip portions shown in the figures cooperate to satisfy siderail gap requirements specified in regulation 2-52.

Figure 29:
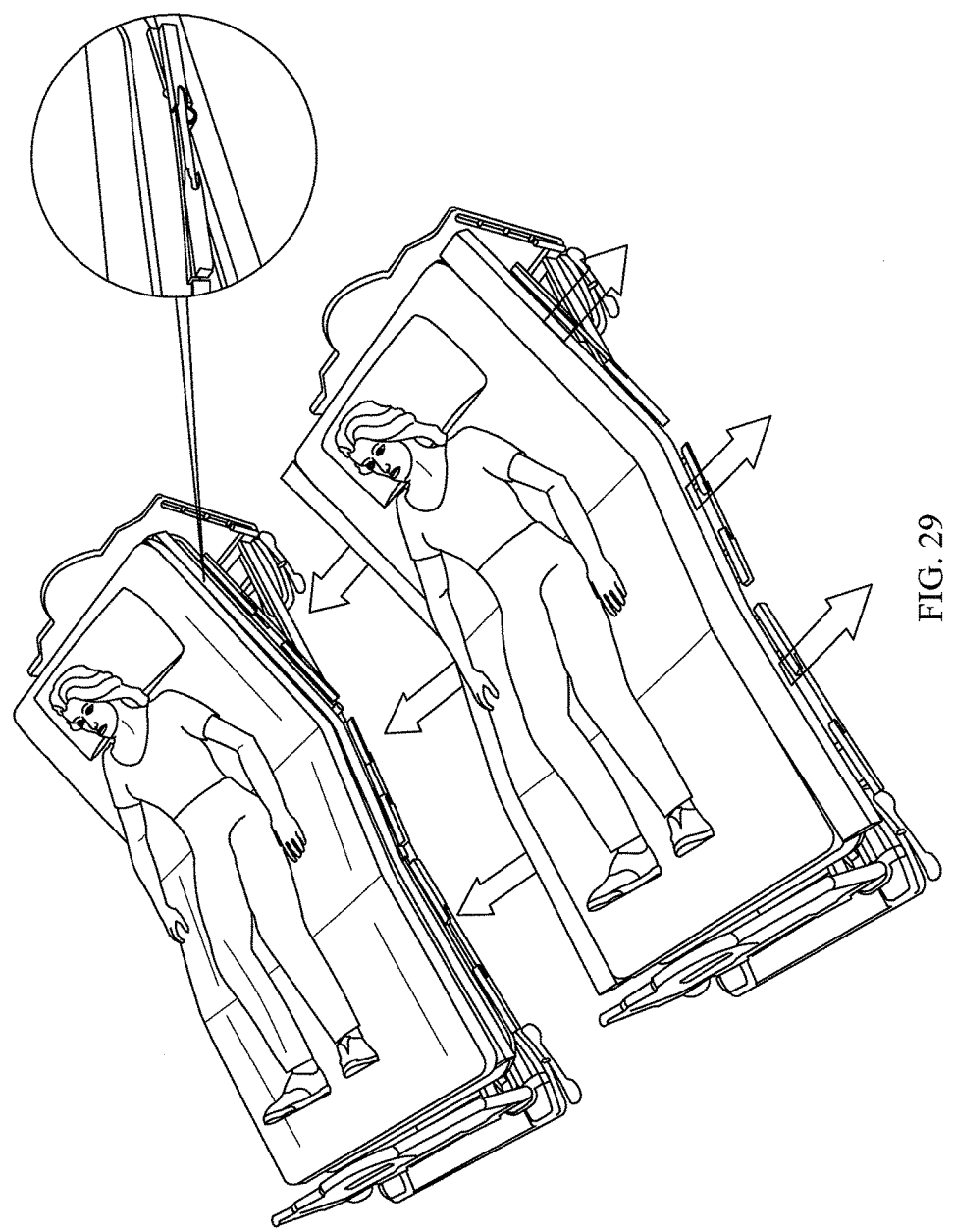
FIG. 29 is a person support apparatus according to another contemplated embodiment of the current disclosure showing a width and/or length adjustable mattress positioned thereon.

In some contemplated embodiments, the person support apparatus 10 supports a person support surface 18 or mattress 18 on the upper frame 16. The person support surface 18 includes a main mattress portion MP1 and extensions EX1 configured to extend from the sides and foot end of the main portion MP1 as shown in FIGS. 29 and 30. The extensions EX1 are coupled to the main portion MP1 via a hinge and are manually moved from a nested or retracted position where two surface of the extensions EX1 are substantially flush with the side and bottom surfaces of the main portion MP1 to an extended or deployed position where a surface of the extensions EX1 are substantially co-planar with the upper surface of the main portion MP1.

In one contemplated embodiment, at least one of the extension and the main portion are composed of foam. In another contemplated embodiment, at least one of the main portion and the extension include a static gas bladder. In another contemplated embodiment, at least one of the main portion and the extension includes an air bladder. The main portion and the extension are enclosed in a cover CV1 (or ticking) including a first chamber where the main portion is positioned and a second chamber were the extension is positioned; the first chamber and the second chamber are separated by the hinge, which in some contemplated embodiments is a stitched seam. The top surface of the main portion is a first length and the bottom surface of the main portion is a second length, which is less than the first length. In one contemplated embodiment, the first length is the second length plus the width of the extension(s). The extensions EX1 are supported on the deck extensions 36 when they are in the extended position. In some contemplated embodiments, the extensions EX1 include a load bearing resin panel that is configured to span the gaps between parts of the deck extensions 36 and provide support to an occupant on the extension EX1.

Figure 36:
FIG. 36 is the person support apparatus of FIG. 34, wherein the light displays a message on the floor to indicate that the user should not exit the person support apparatus.
Figure 37:
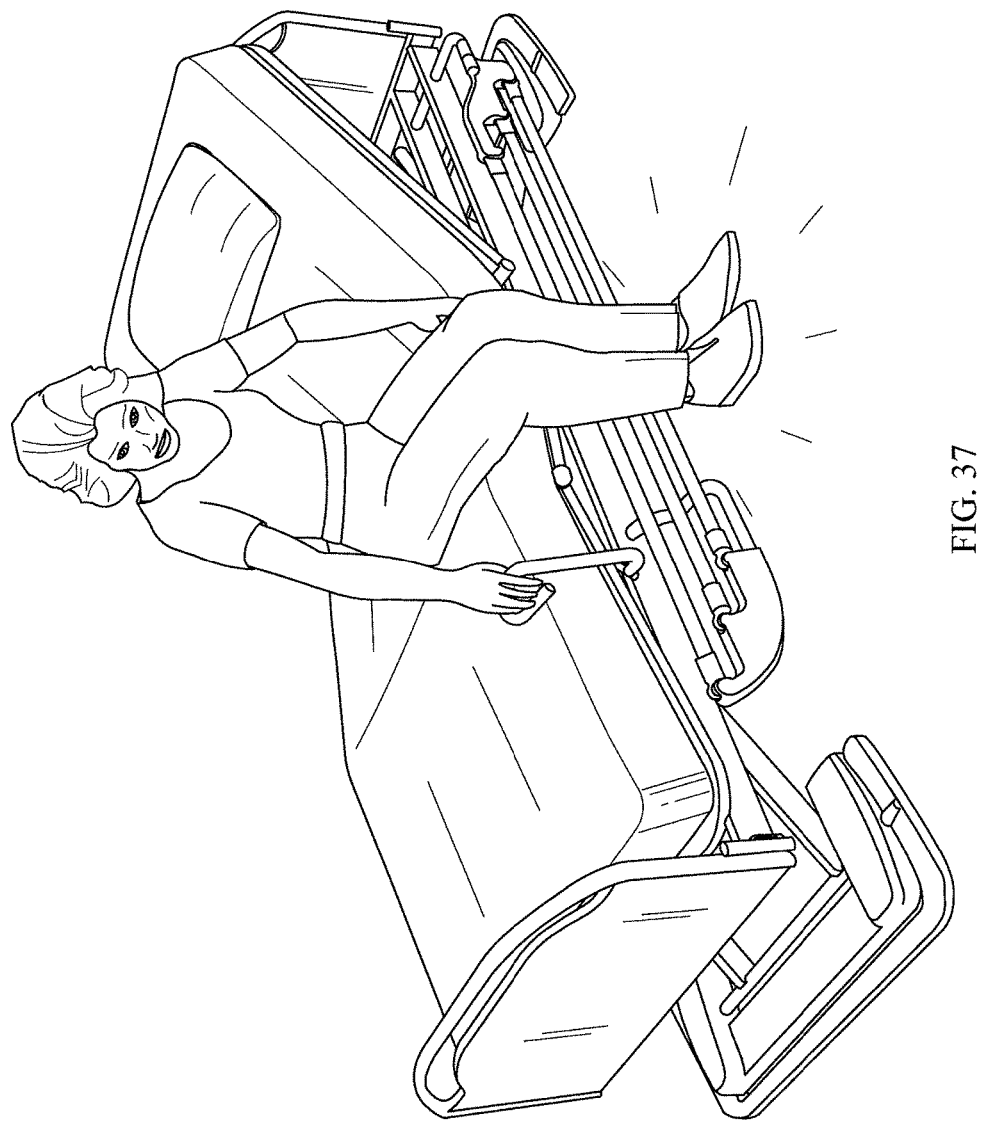
FIG. 37 is the person support apparatus of FIG. 34, wherein the light is a standard night light.
Figure 38:
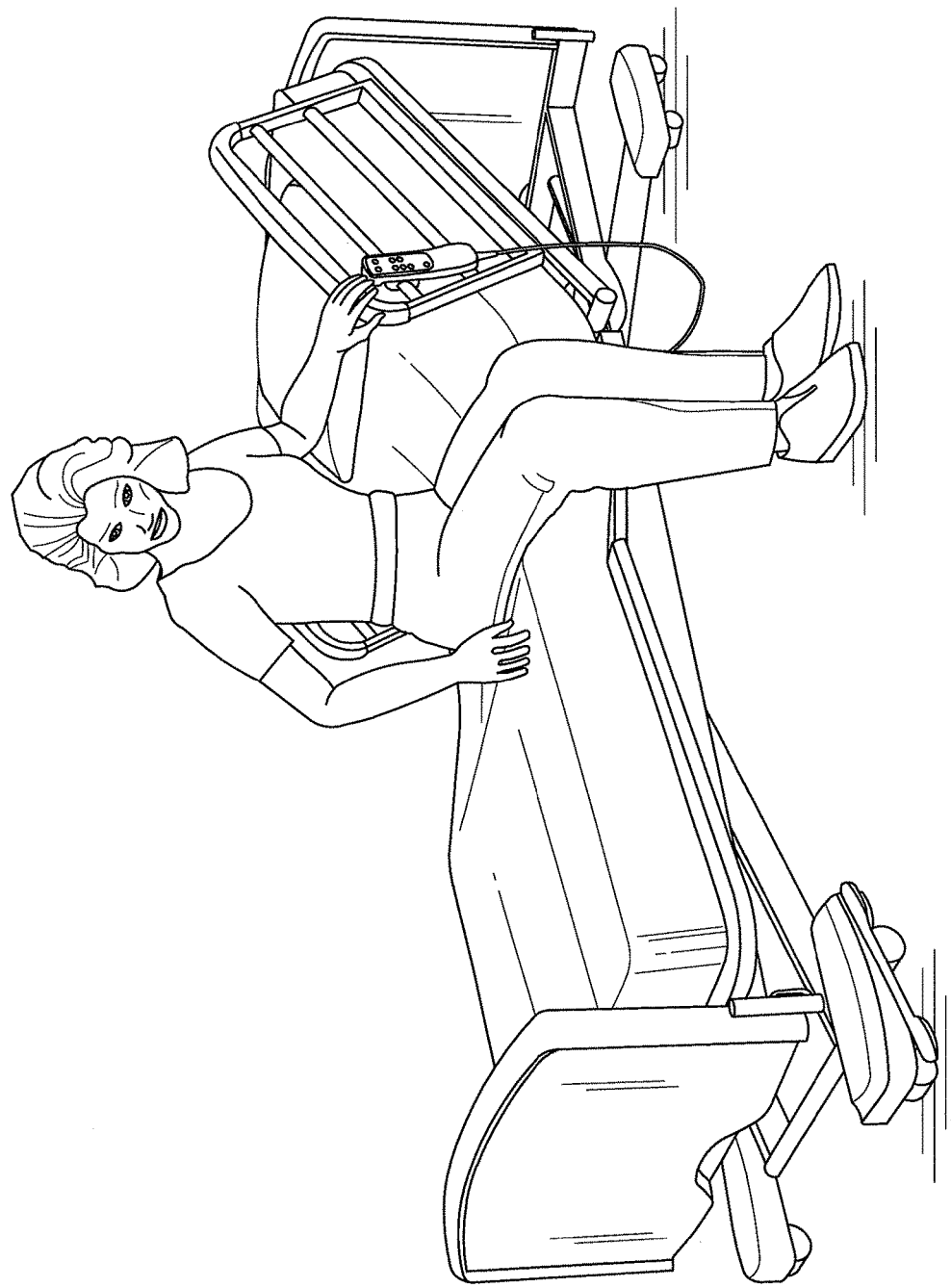
FIG. 38 is a person support apparatus according to another contemplated embodiment of the current disclosure.
Figure 39:
FIG. 39 is a person support apparatus according to another contemplated embodiment of the current disclosure.
Figure 40:
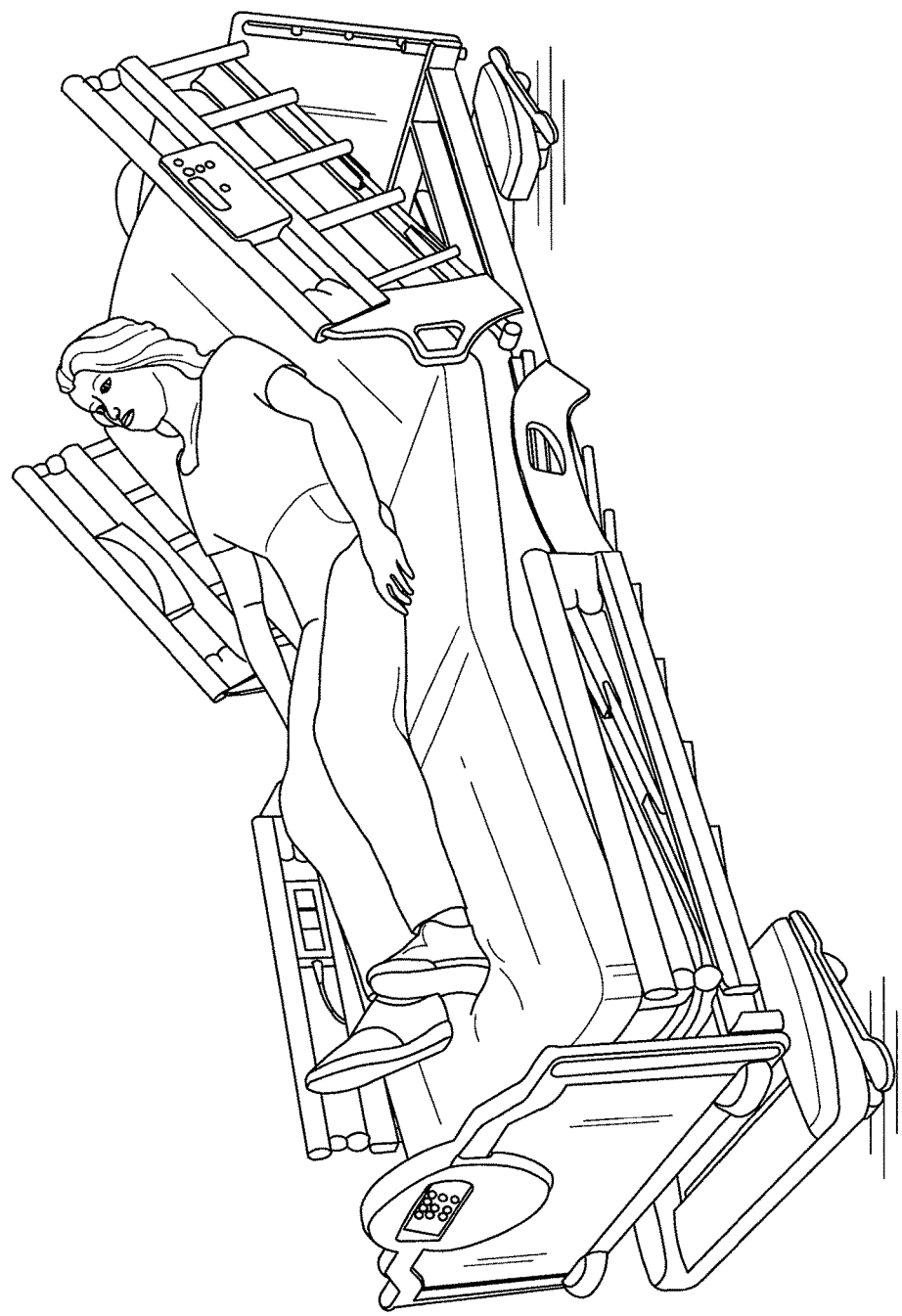
FIG. 40 is a person support apparatus according to another contemplated embodiment of the current disclosure.
Figure 41:
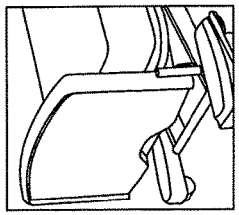
FIG. 41 is a person support apparatus according to another contemplated embodiment of the current disclosure showing different configurations of endboards.
Figure 41:
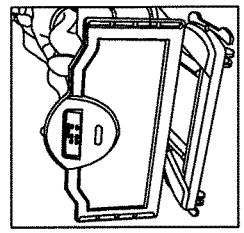
Figure 41:
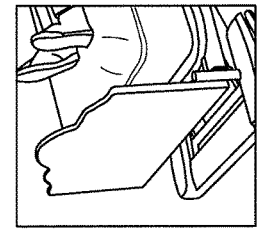
Figure 41:
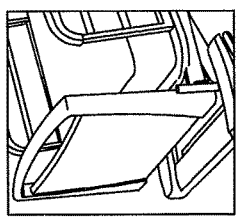
Figure 41:
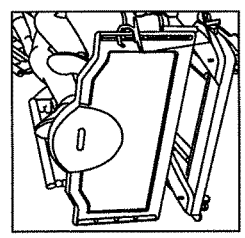
Figure 41:
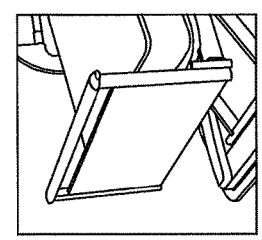
Figure 41:
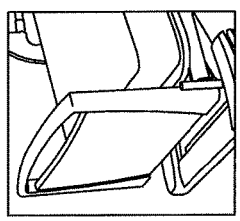
Figure 41:
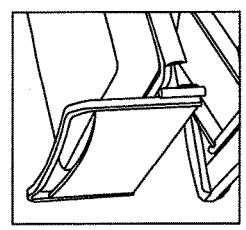
Figure 41:
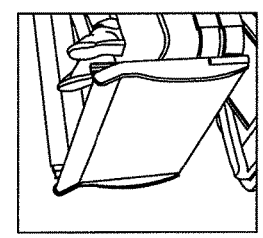
Figure 41:
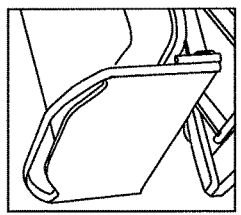
Figure 41:
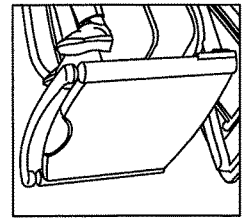
Figure 41:
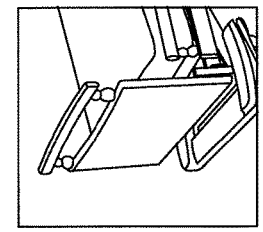
Figure 41:
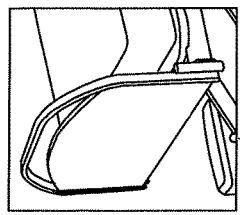
Figure 41:
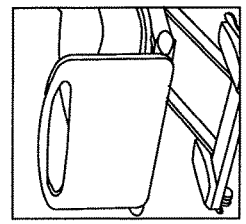
Figure 41:
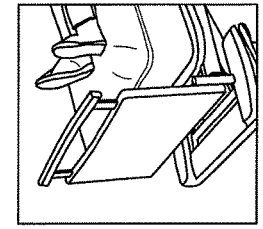
Figure 42:
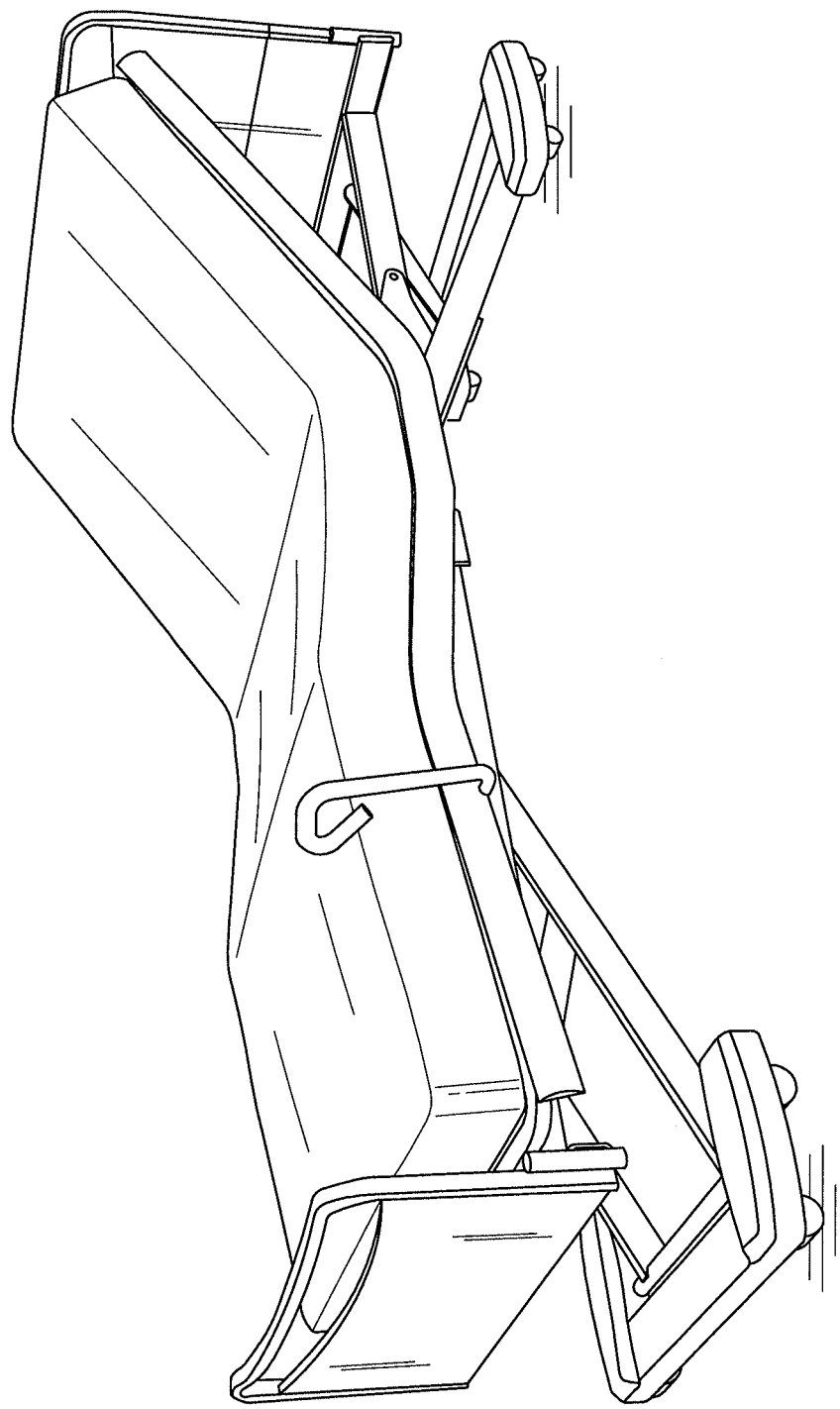
FIG. 42 is a person support apparatus according to another contemplated embodiment of the current disclosure.
Figure 43:
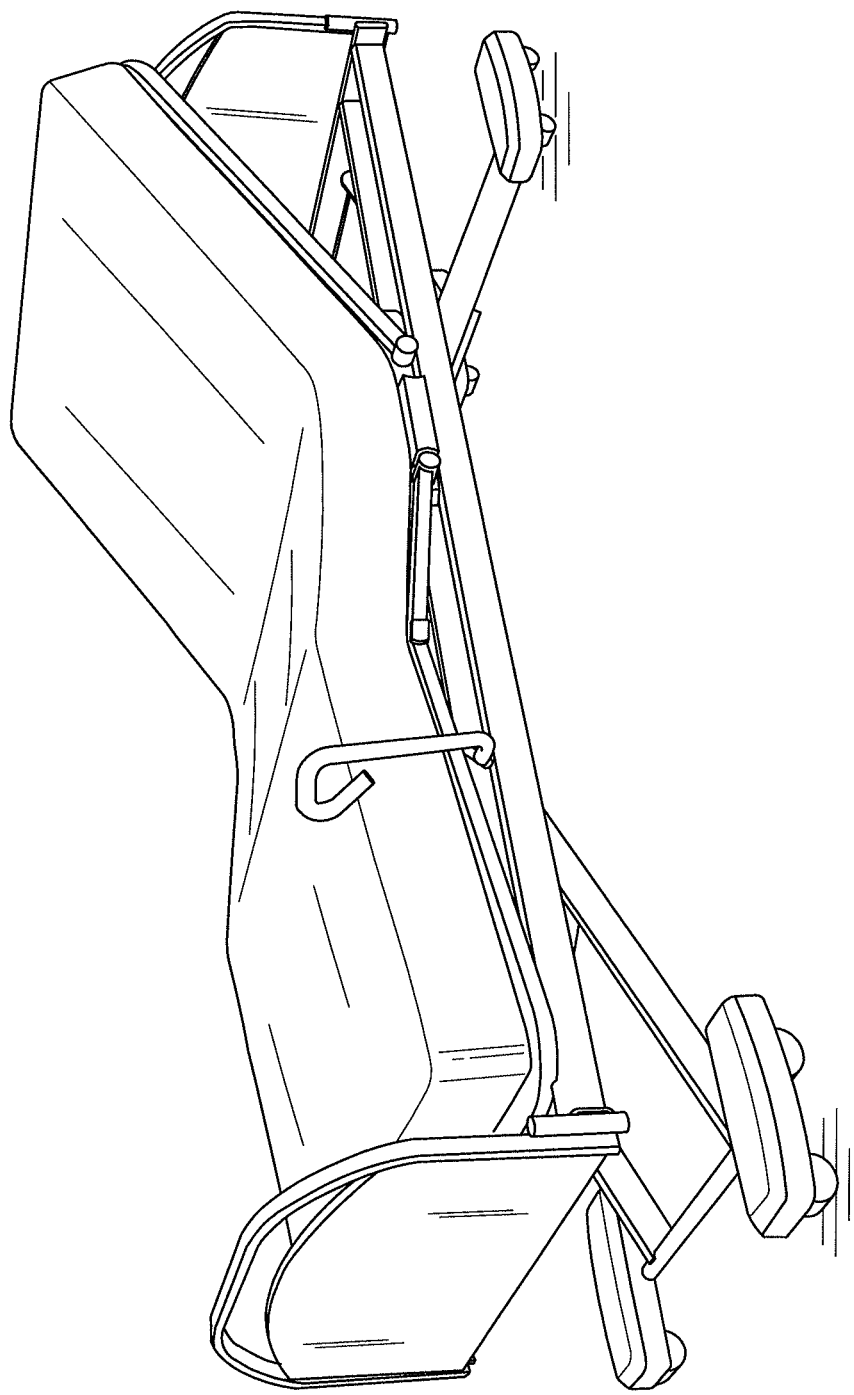
FIG. 43 is a person support apparatus according to another contemplated embodiment of the current disclosure.
Figure 44:
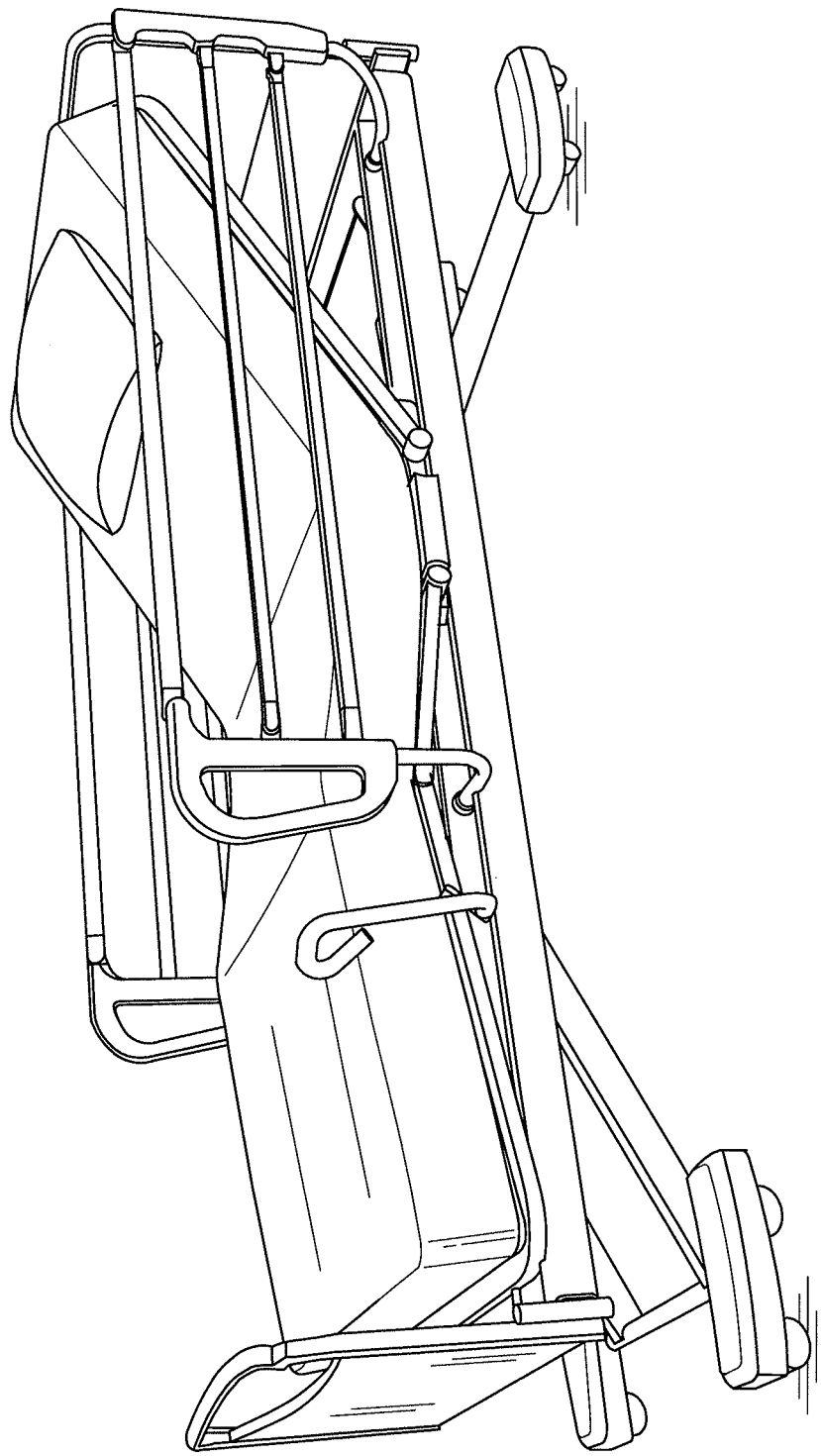
FIG. 44 is a person support apparatus according to another contemplated embodiment of the current disclosure.
Figure 45:
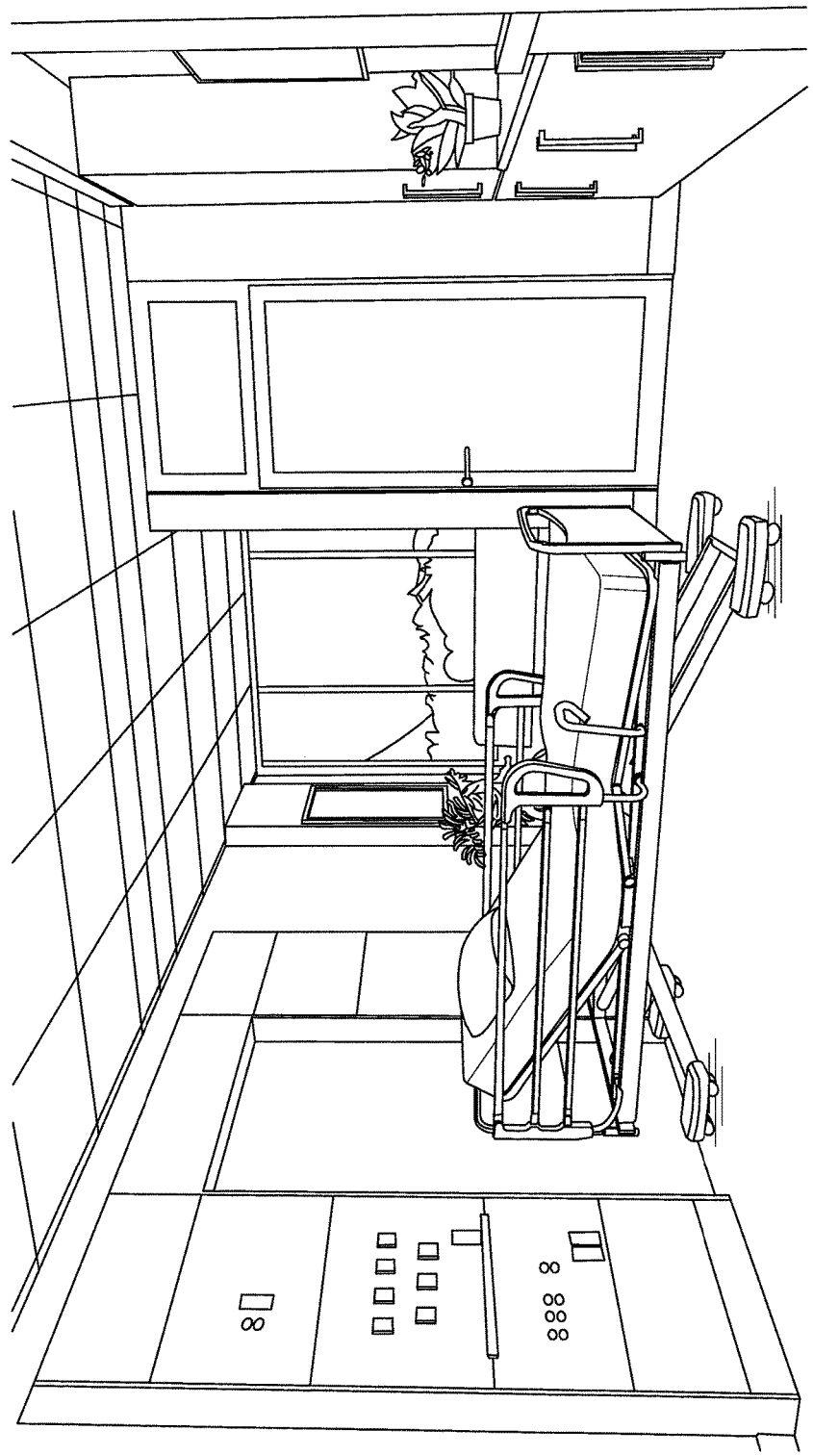
FIG. 45 is a person support apparatus according to another contemplated embodiment of the current disclosure.
Figure 46:
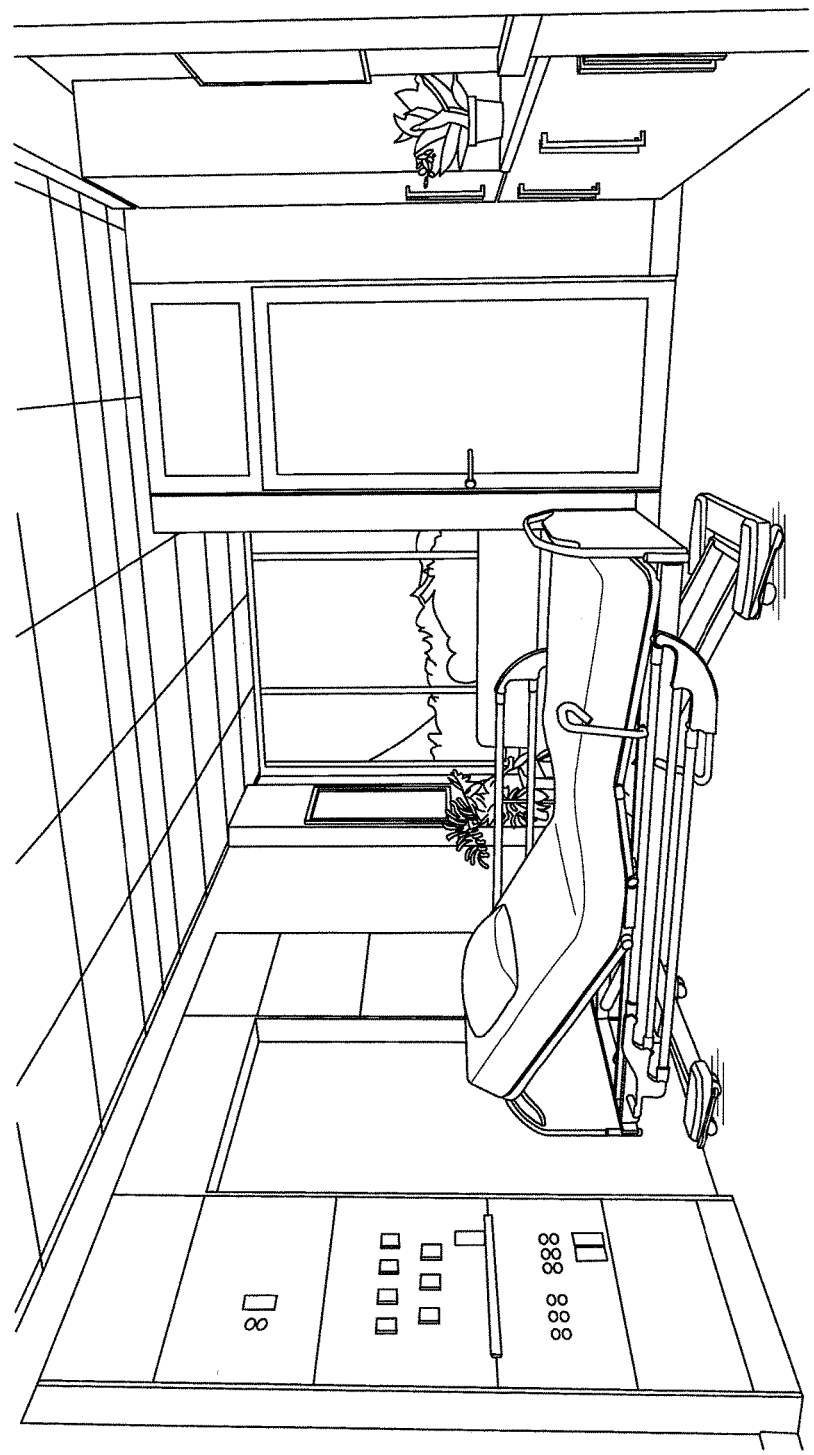
FIG. 46 is a person support apparatus according to another contemplated embodiment of the current disclosure.
Figure 47:
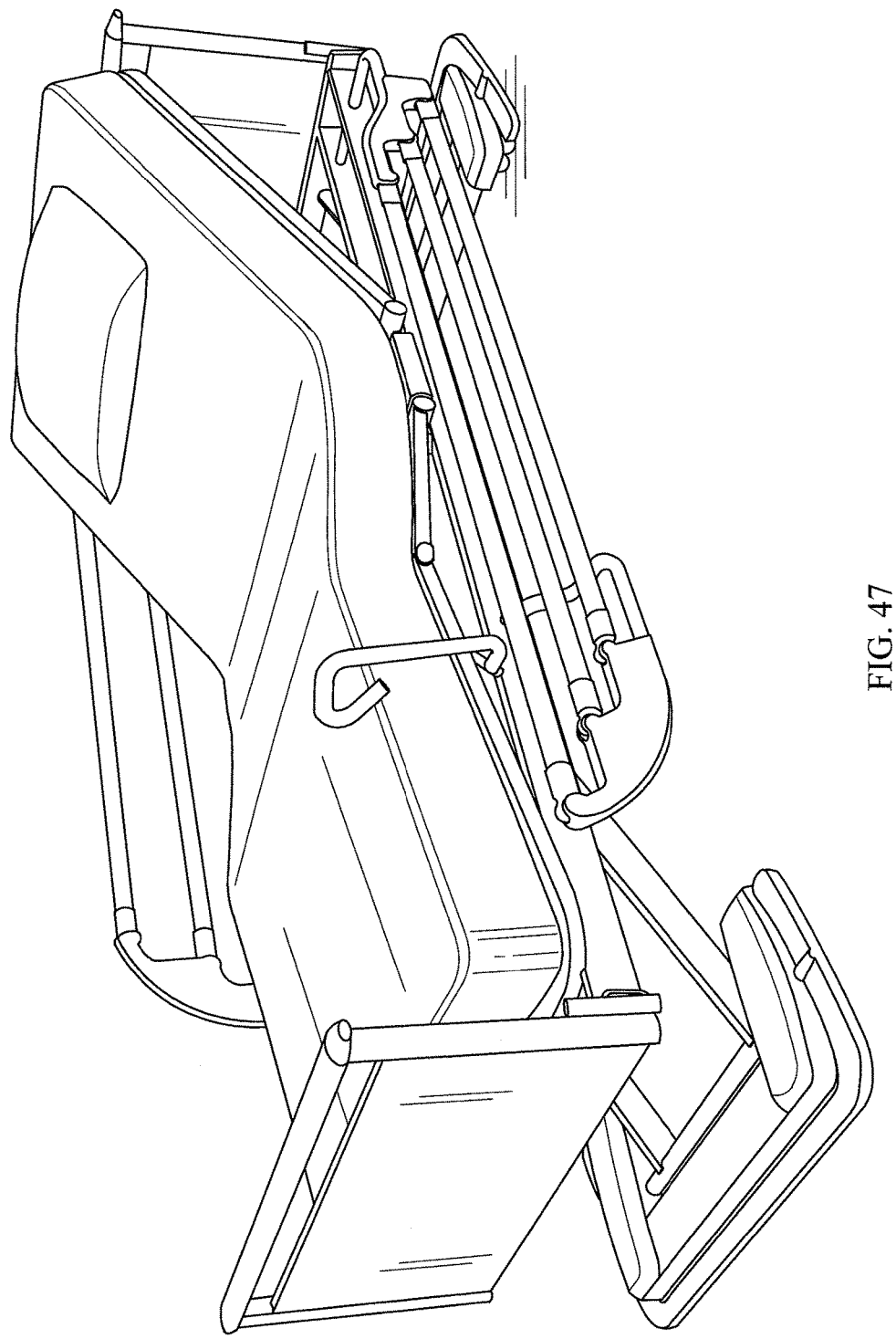
FIG. 47 is a person support apparatus according to another contemplated embodiment of the current disclosure.
Figure 48:
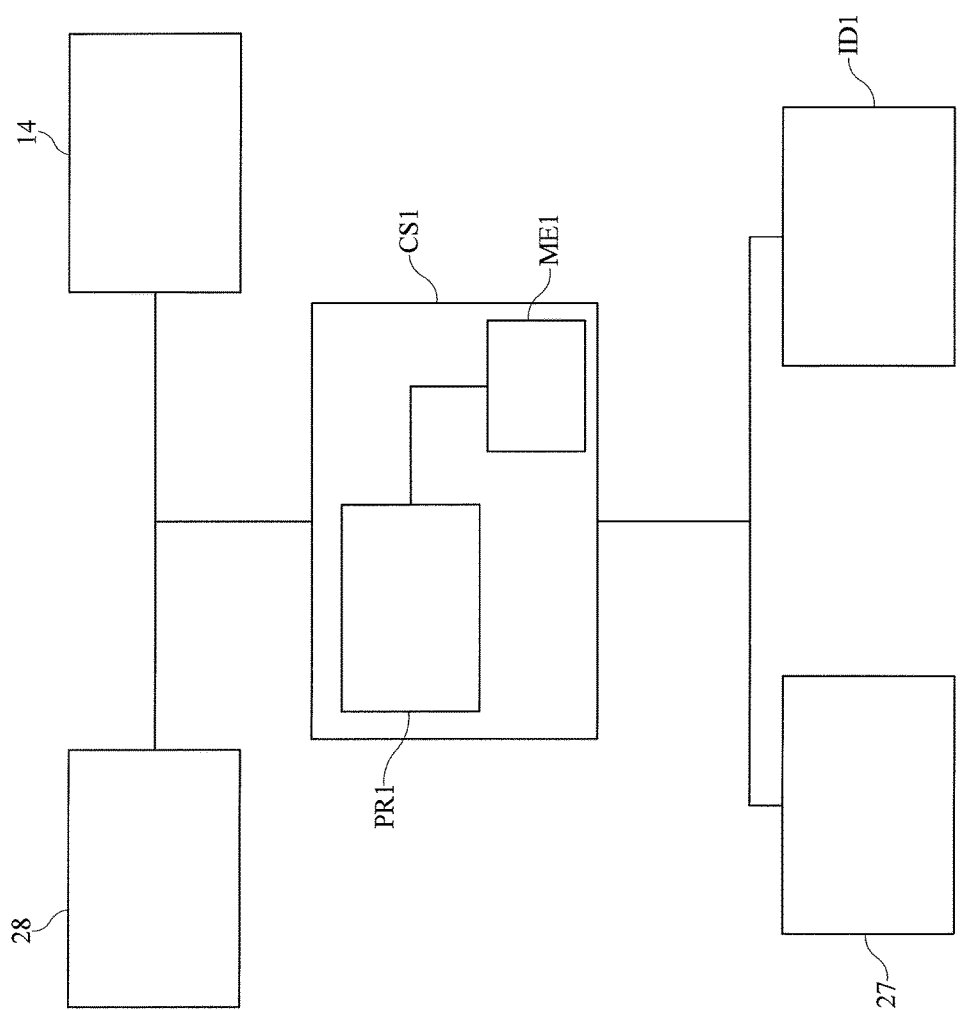
FIG. 48 is a person support apparatus according to another contemplated embodiment of the current disclosure showing the control system.

The night light 27 is coupled to the upper frame 16 and is configured to shine a light on the floor when the ambient lighting is below a predetermined threshold as shown in FIGS. 33-36. In one illustrative embodiment, the night light 27 is configured to inform a person as to when the upper frame 16 is at a height where the person can egress the bed more easily. In one illustrative embodiment, the light is amber colored when the person should not exit the person support apparatus 10 and green when the person should exit the person support apparatus 10. In another illustrative embodiment, the night light 27 also displays a message on the floor to inform the occupant as to when they should egress from the person support apparatus 10. In one contemplated embodiment, the message includes words, such as, "DO NOT EXIT." In other contemplated embodiments, the message includes images, such as, a stop sign, a nurse call icon, a caution symbol (triangle with an exclamation point within the triangle). In some contemplated embodiments, the messages are displayed in multiple colors. The messages can be formed by filtering the light produced by the night light so that only the message shines through the filter. In some contemplated embodiments, the light is filtered so that the message is outlined on the floor. The filter can be implemented digitally so that certain lights in an array of lights are activated, or by illuminating a light positioned behind a stencil that outlines the shape of the message. In some contemplated embodiments, the night light is integrated into the grip handle coupled to the upper frame as shown in FIG. 36 and lights up the grip to indicate the status of the person support apparatus.

Figure 17:
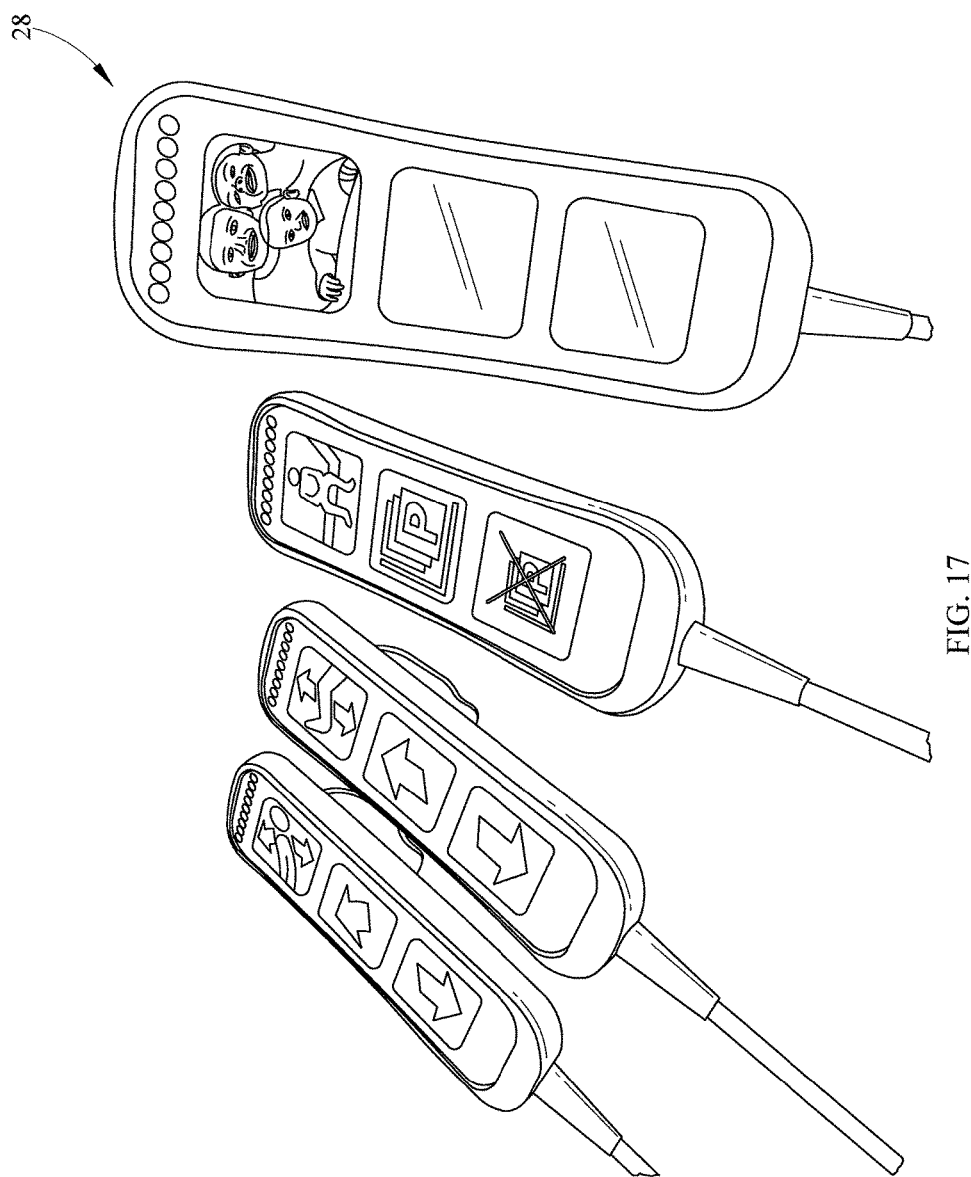
FIG. 17 is a pendant according to another contemplated embodiment of the current disclosure including screen keys.
Figure 18:
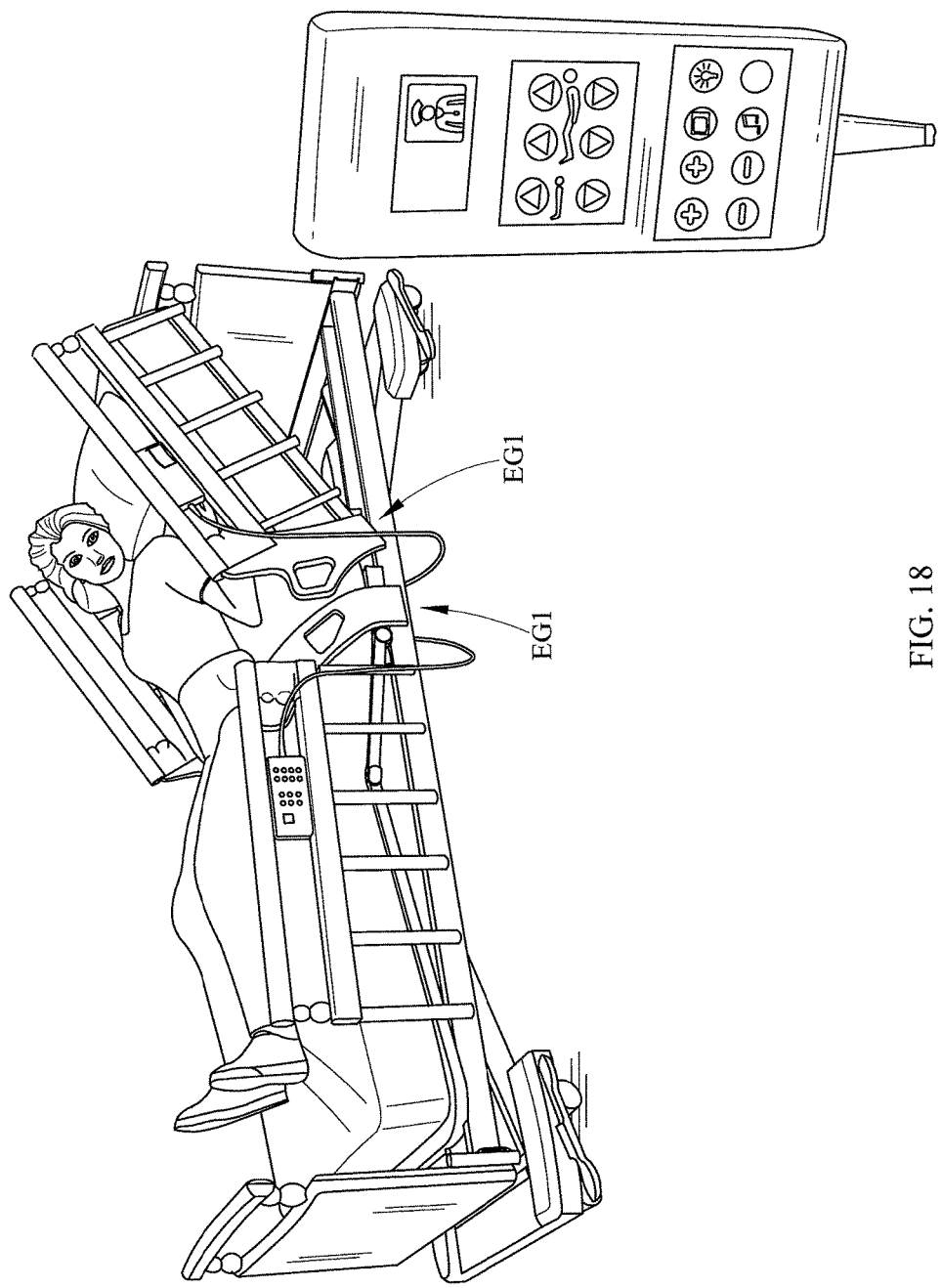
FIG. 18 is a person support apparatus according to another contemplated embodiment of the current disclosure.
Figure 19:
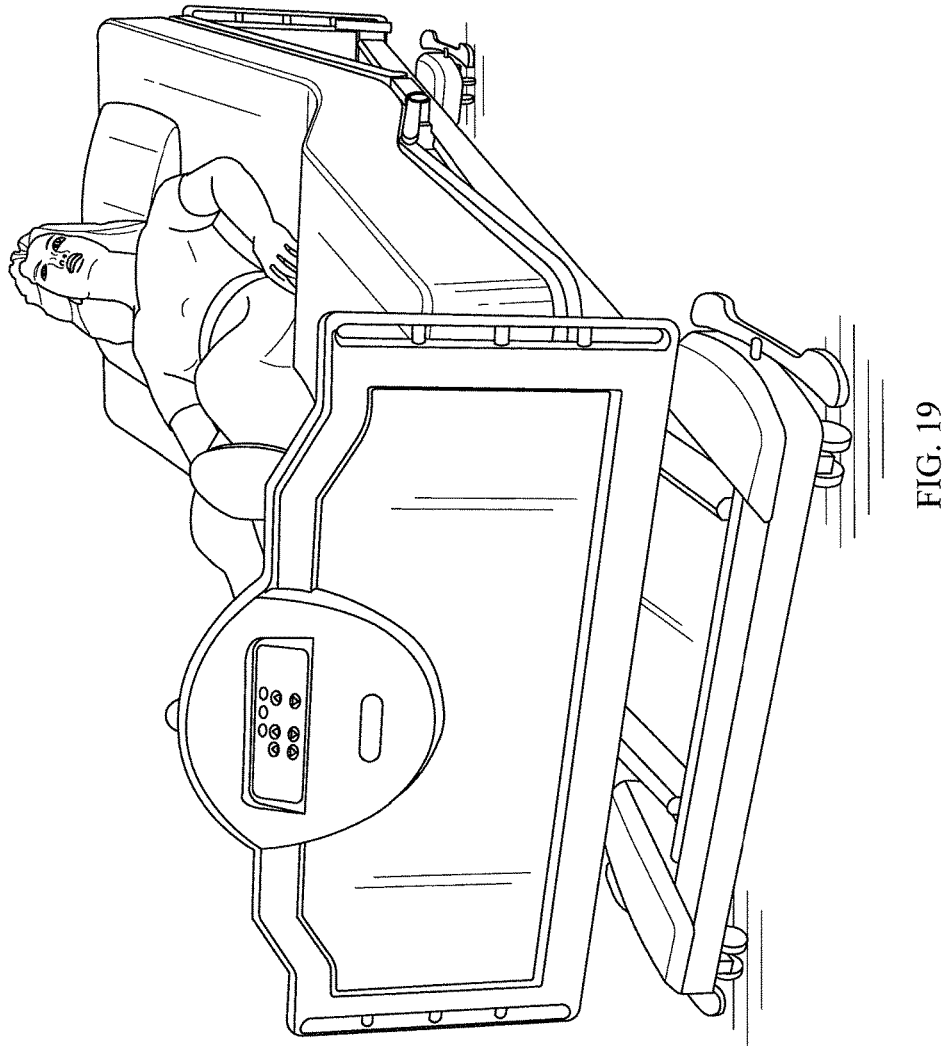
FIG. 19 is a person support apparatus according to another contemplated embodiment of the current disclosure.
Figure 20:
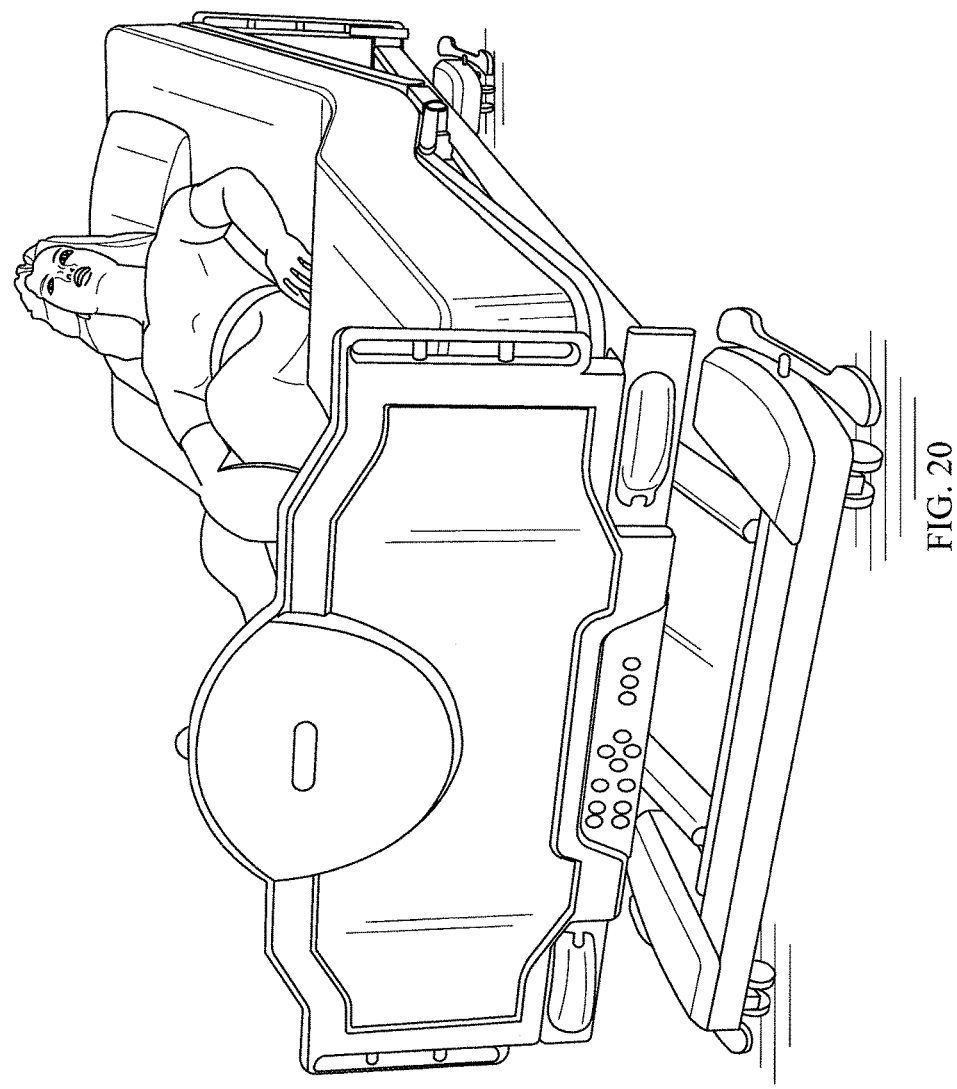
FIG. 20 is a person support apparatus according to another contemplated embodiment of the current disclosure showing status indicating lights coupled to the foot end of the person support apparatus.
Figure 21:
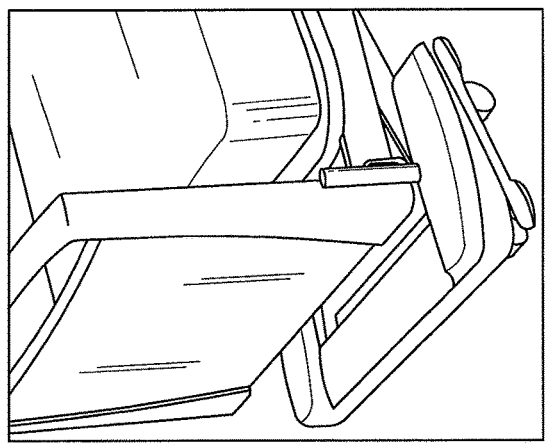
FIG. 21 is the status indicating lights of FIG. 20 according to another contemplated embodiment of the current disclosure.
Figure 21:
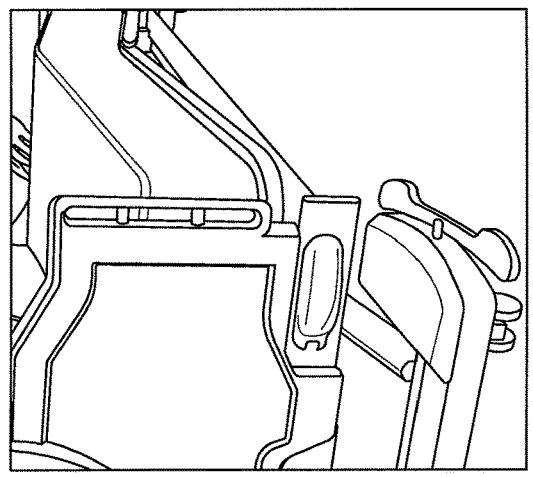
Figure 21:
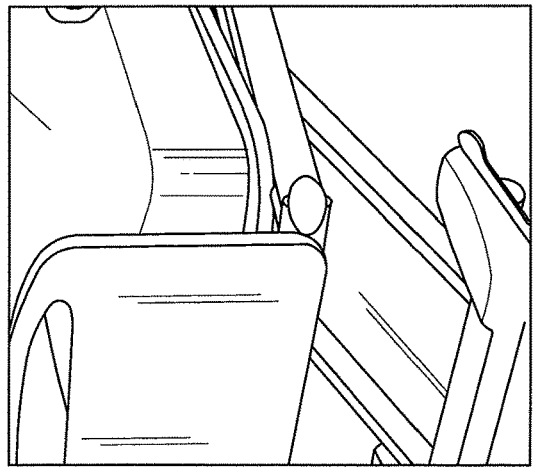
Figure 22:
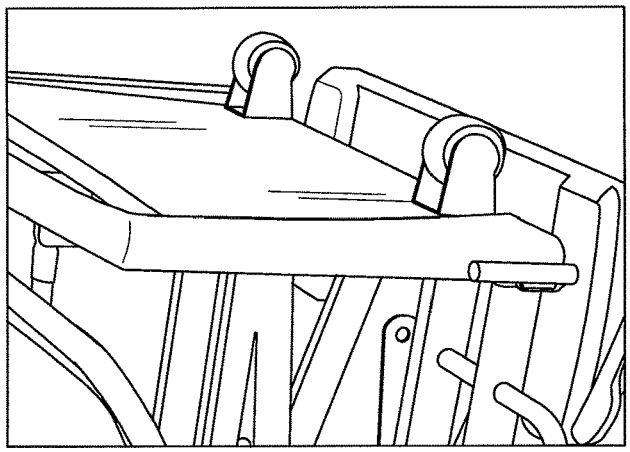
FIG. 22 is a person support apparatus according to another contemplated embodiment of the current disclosure.
Figure 22:
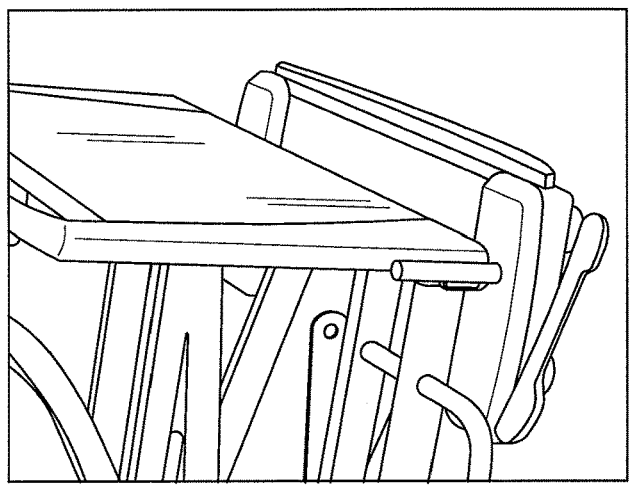
Figure 22:
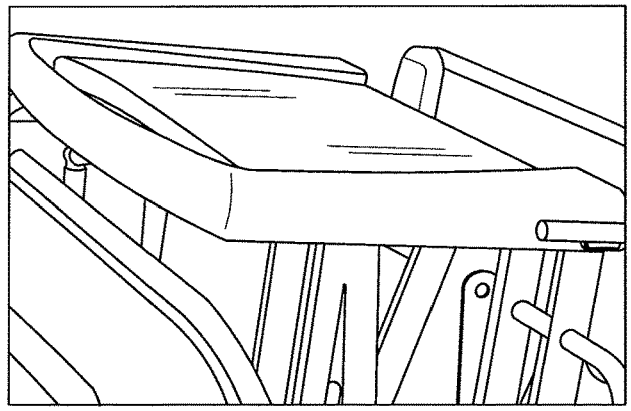
Figure 23:
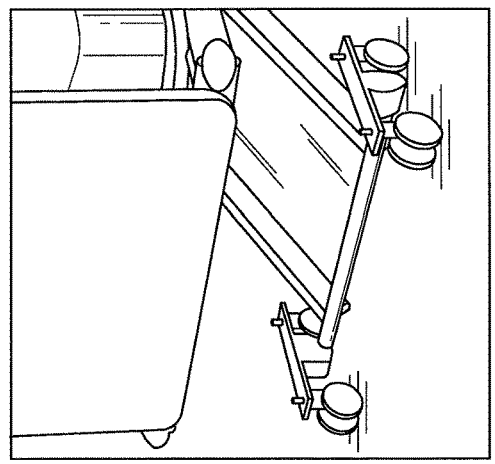
FIG. 23 is a person support apparatus according to another contemplated embodiment of the current disclosure.
Figure 23:
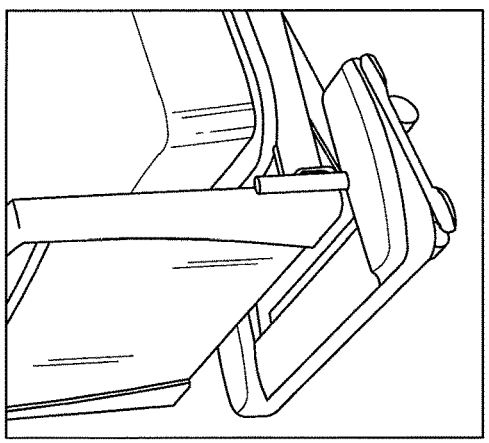
Figure 23:
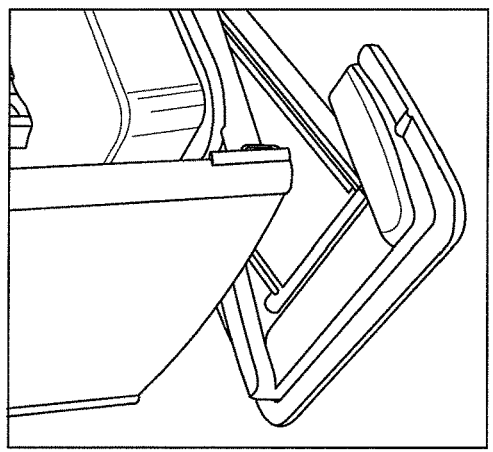
Figure 24:
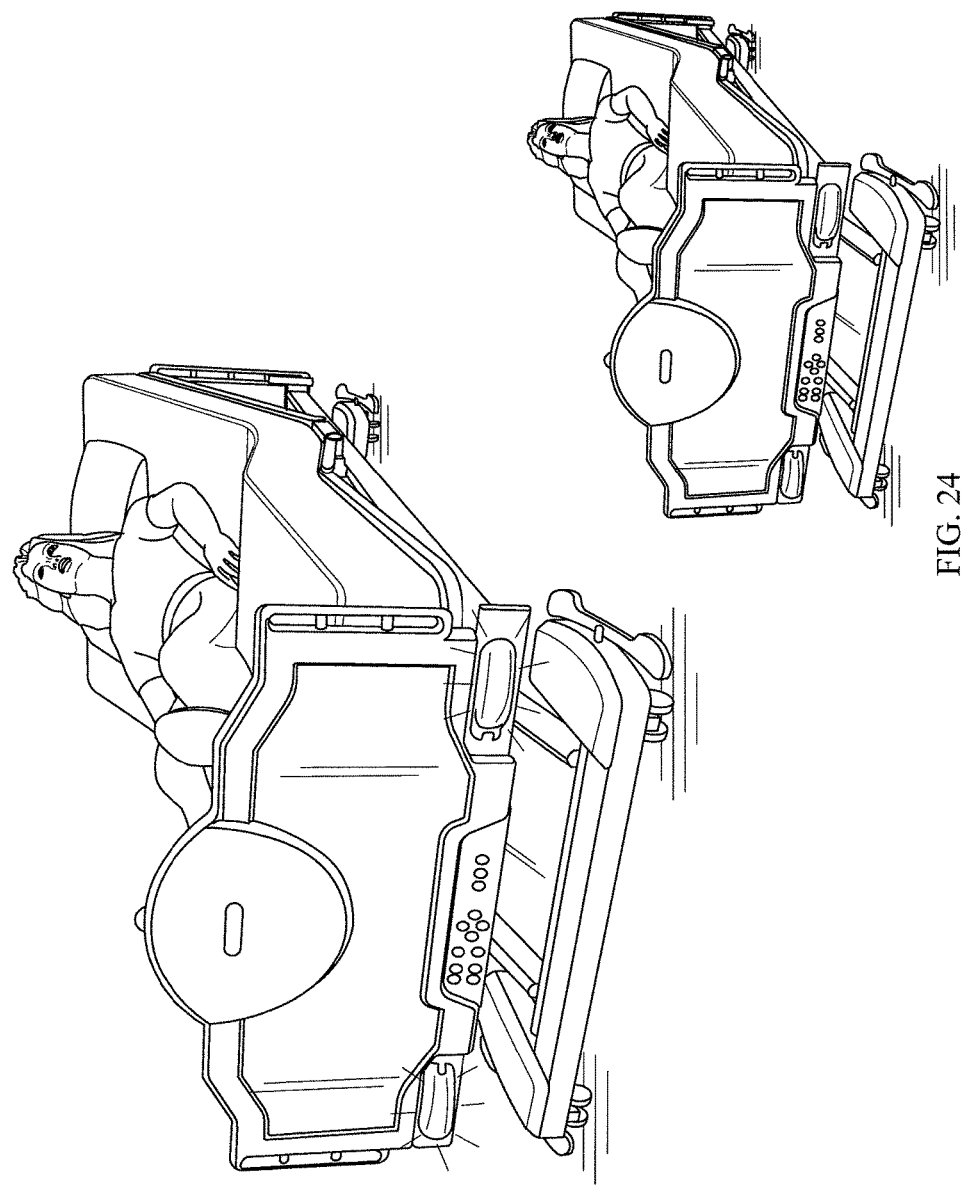
FIG. 24 is the status indicating lights of FIG. 20 according to another contemplated embodiment of the current disclosure.
Figure 25:
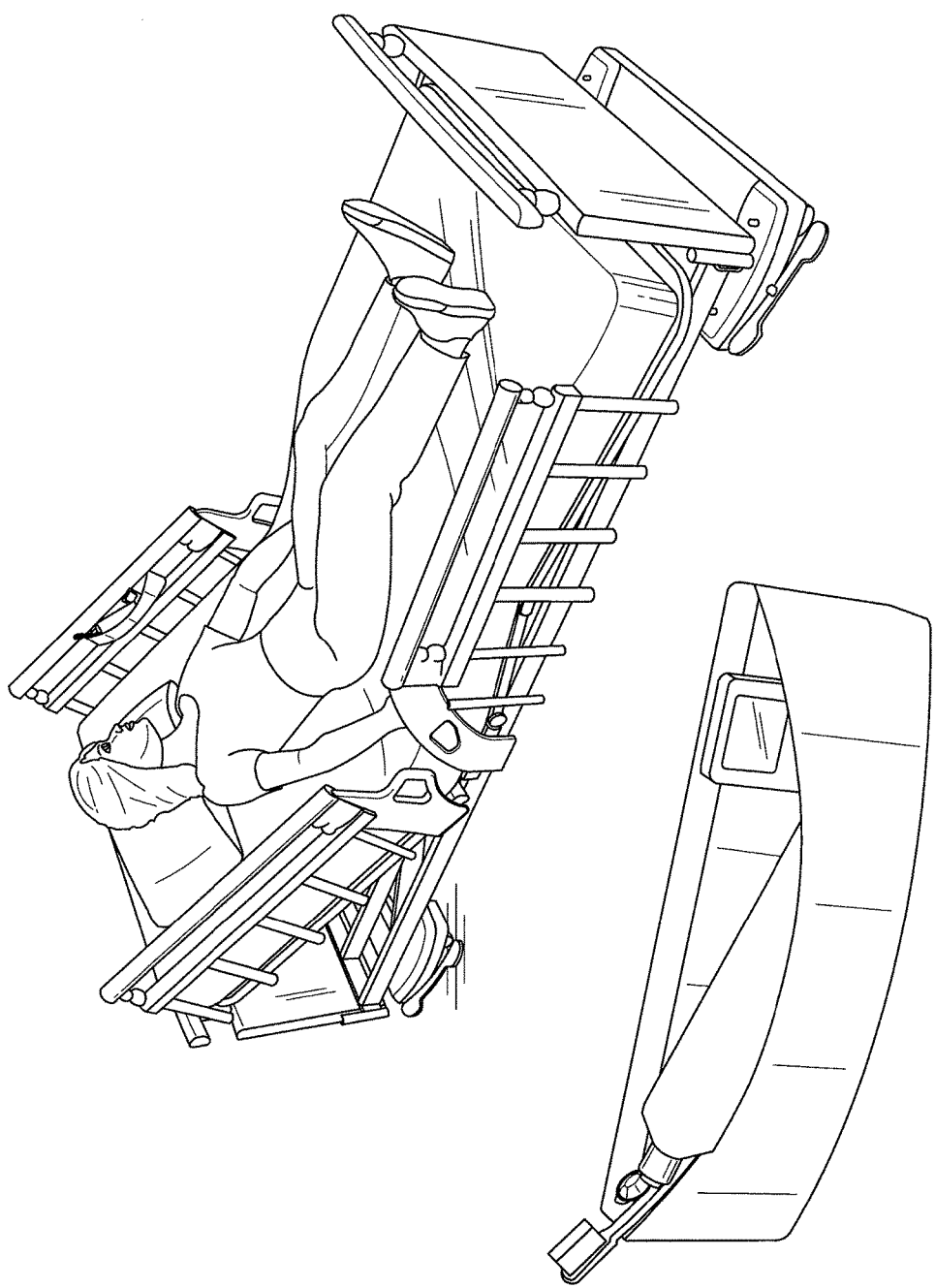
FIG. 25 is a person support apparatus according to another contemplated embodiment of the current disclosure showing a storage area for storing personal items configured to be coupled to a siderail.
Figure 26:
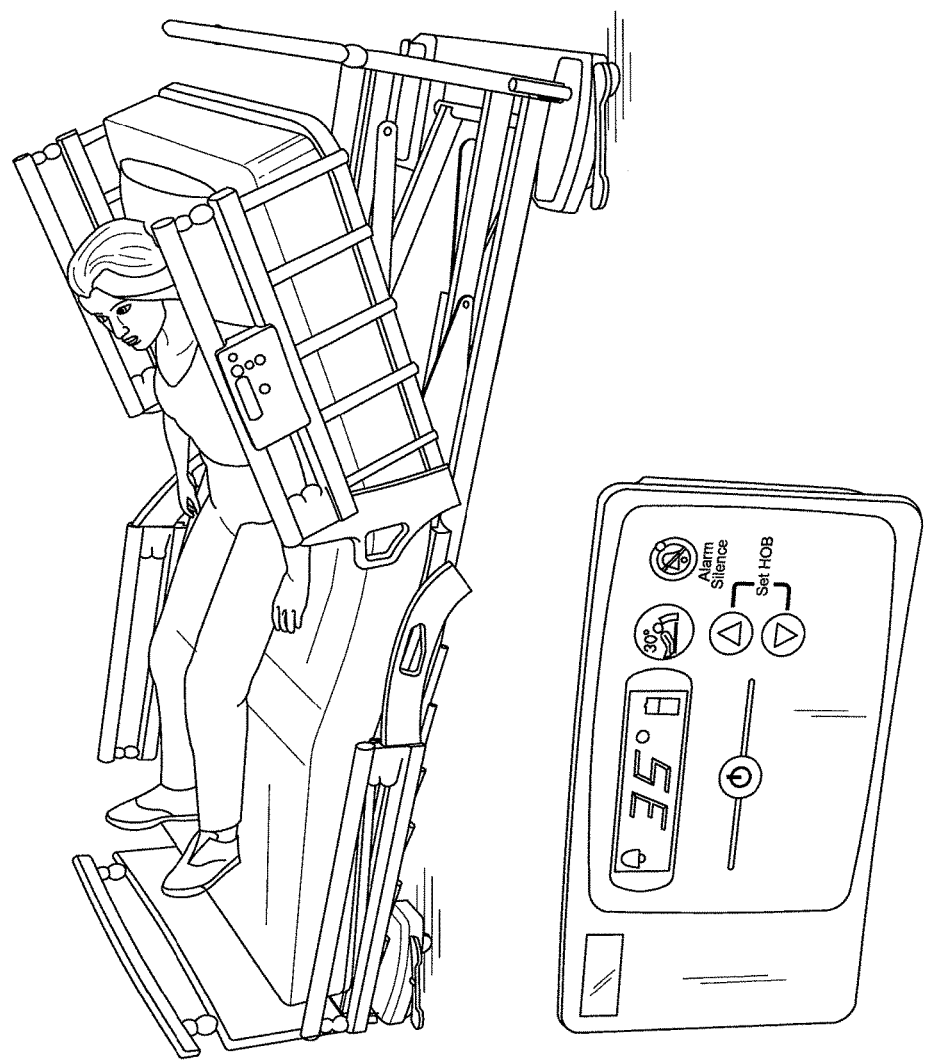
FIG. 26 is a person support apparatus according to another contemplated embodiment of the current disclosure showing a pendant configured to be coupled to the siderail of the person support apparatus and configured to digitally display the angle of the head end of the bed with respect to horizontal and alarm when the angle drops below a predetermined threshold.
Figure 27:
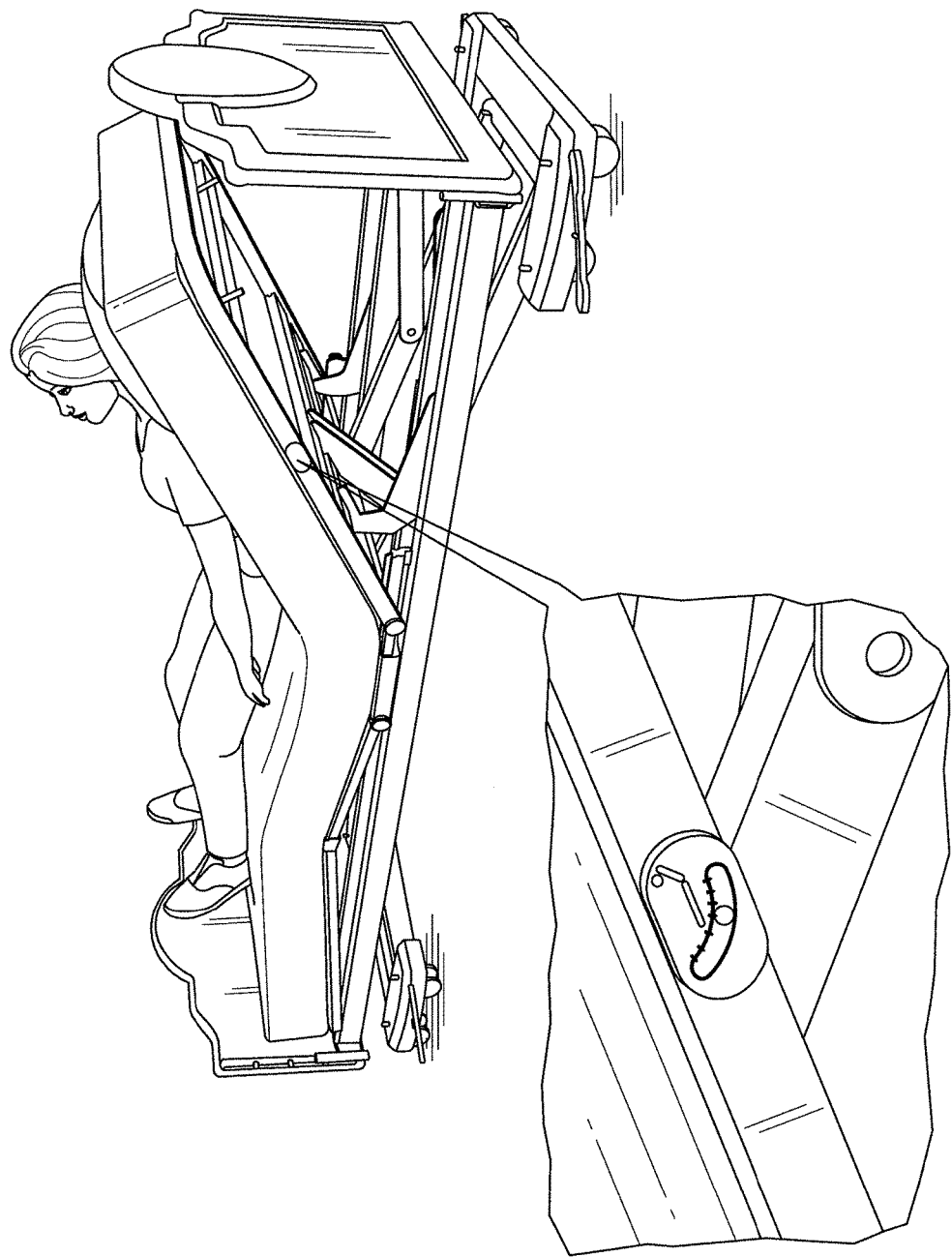
FIG. 27 is a person support apparatus according to another contemplated embodiment of the current disclosure showing an inclinometer coupled to the upper frame with a rolling element configured to move within a housing to indicate the angle of the head end of the bed with respect to horizontal.
Figure 28:
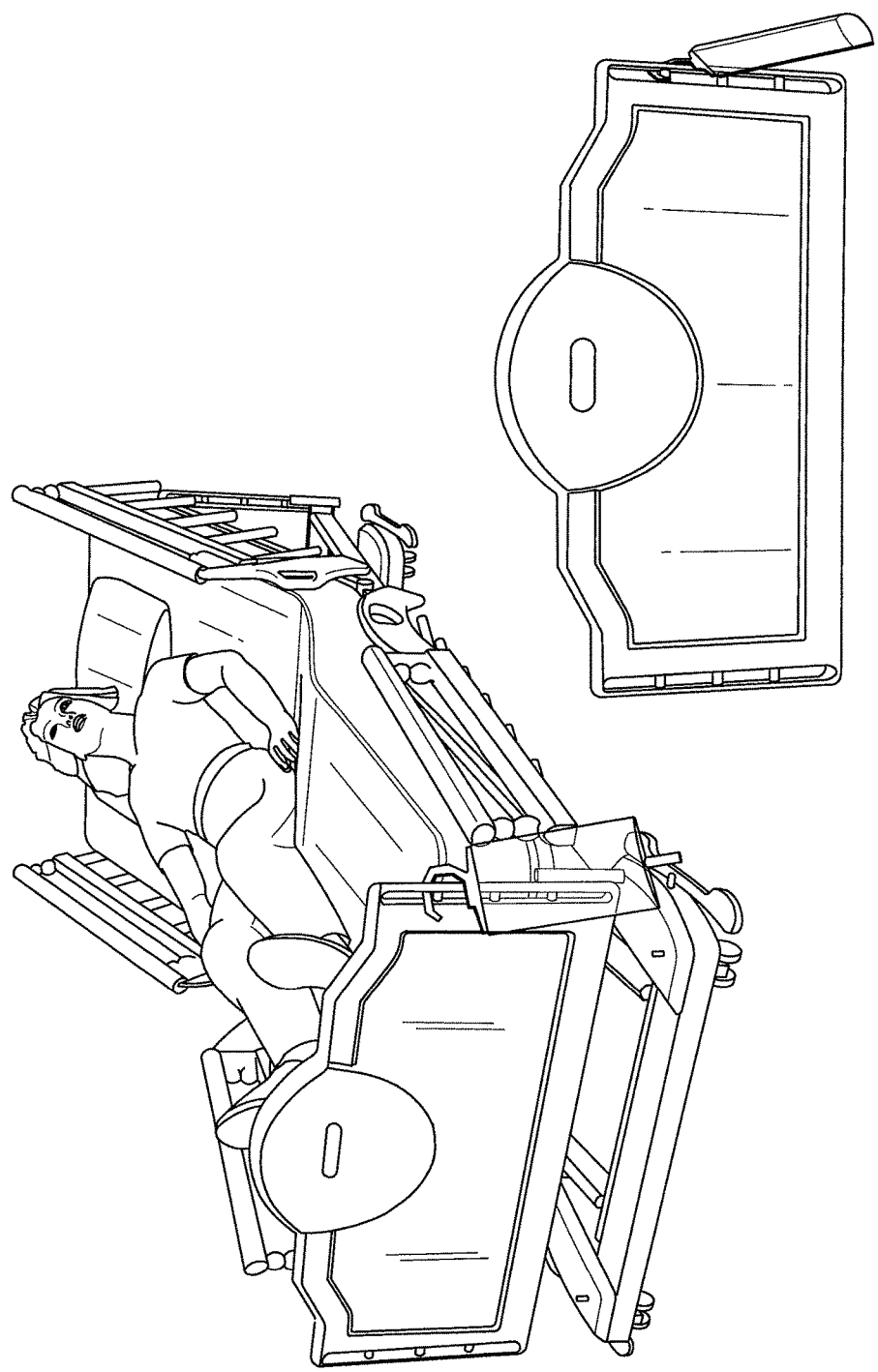
FIG. 28 is a person support apparatus according to another contemplated embodiment of the current disclosure.

The pendant 28 is configured to control at least one function of the person support apparatus 10. In one illustrative embodiment, the pendant 28 includes high resolution, full color displays, such as, TFT ScreenKeys, which can display images thereon that the user can press to select the function they wish the bed to perform as shown in FIG. 17. The ScreenKeys, which can be found at www.screenkeys.com and feature 128*128 pixel resolution, an SPI interface, full color imaging, bitmap addressable—high level commands, internal character generation, 7 lines with 9 characters per line, user downloadable font support, 10 fps refresh rate, and low profile, among other things. The user can select different modes on the controller pressing the top key TK1, which changes the mode indicator MI1 and the two bottom keys BK1 or action keys BK1 to control different functions of the person support apparatus 10. In some contemplated embodiments, the keys display an image of a family member of the patient to make the pendant seem less intimidating.

The control system CS1 is electrically coupled to the night-light 27, the pendant 28, the lift system 14, and an input device ID1. The control system CS1 includes a processor PR1 and memory ME1 that stores instructions to be executed by the processor PR1. The input device ID1 is configured to provide an input corresponding to the status of the person support apparatus 10, such as, for example, whether the upper frame is at a predetermined egress height. In some contemplated embodiments, the input device ID1 is an electronic medical record system that displays messages to the occupant or caregiver to remind them to perform actions or seek assistance before performing actions. In another contemplated embodiment, the input device is a remote caregiver station that allows the caregiver to provide information to the occupant remotely, such as, asking the occupant to remain in bed until a nurse can assist them with exiting the person support apparatus. In yet another contemplated embodiment, the input device is a sensor that, in one example, senses the distance between the upper frame and the floor. In some contemplated embodiments, the control system controls the operation of the night light to display messages on the floor in accordance with the input from the input device.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless can not be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles can have been presented, they need not be utilized in combination, and various combinations of inventive aspects and principles are possible in light of the various embodiments provided above.

The invention claimed is:

1. A hospital bed comprising:
   a frame configured to support an occupant;

a first indicator coupled to the frame and configured to emit light onto a floor adjacent the frame to produce an icon on the floor;

a second indicator including a light integrated into a grip that is graspable by the occupant while exiting the hospital bed, the grip being coupled to the frame, the second indicator being operable to shine light only through an illuminable surface of the grip and not through a non-illuminable surface of the grip that faces oppositely from the illuminable surface; and a controller coupled to the frame and configured to control operation of the first and second indicators, wherein the controller causes the first indicator and the second indicator to illuminate to provide information relating to occupant exit from the frame.

2. The hospital bed of claim 1, wherein the light emitted from the first indicator produces the icon on the floor beyond a foot print of the frame.

3. The hospital bed of claim 1, wherein the icon includes a symbol.

4. The hospital bed of claim 3, wherein the symbol includes a triangle with an exclamation point positioned within the triangle.

5. The hospital bed of claim 3, wherein the icon includes a circle with a backward slash passing through the circle.

6. The hospital bed of claim 1, wherein the icon is displayed in a plurality of colors.

7. The hospital bed of claim 1, wherein the icon is displayed in amber light.

8. The hospital bed of claim 1, wherein the icon is displayed in green light.

9. The hospital bed of claim 1, wherein the icon is displayed in red light.

10. The hospital bed of claim 1, wherein the light emitted by the first indicator is filtered so that the light passing through excludes a shape of the icon.

11. The hospital bed of claim 1, wherein the light emitted by the first indicator is filtered so that the light passing through includes the shape of the icon.

12. The hospital bed of claim 1, wherein the frame includes a base frame and an upper frame movably supported above the base frame and wherein the icon indicates to the user whether the upper frame is at a predetermined egress height relative to the base frame.

13. The hospital bed of claim 1, wherein the icon includes an image of a nurse call symbol.

14. The hospital bed of claim 1, wherein the first indicator is coupled to an upper frame of the person support apparatus.

15. The hospital bed of claim 1, wherein the light emitted by the first indicator is directed toward a portion of the floor adjacent to a side of the frame.

16. The hospital bed of claim 1, wherein the icon indicates a status of the person support apparatus.

17. The hospital bed of claim 1, further comprising an input device and the control system being configured to receive an input from the input device and to control the operation of the first and second indicators based on the input.

18. The hospital bed of claim 17, wherein the input is indicative of a status of the hospital bed.

19. The hospital bed of claim 17, wherein the input device comprises an electronic medical record system in communication with the controller.

20. The hospital bed of claim 17, wherein the input device comprises a remote caregiver station in communication with the controller.

* * * * *